(12) United States Patent
Ponomarev et al.

(10) Patent No.: US 6,582,930 B1
(45) Date of Patent: Jun. 24, 2003

(54) PORPHYRIN COMPOUNDS, THEIR CONJUGATES AND ASSAY METHODS BASED ON THE USE OF SAID CONJUGATES

(75) Inventors: Gelii Vasilevich Ponomarev, Moscow (RU); Dmitry Vladimirovich Yashunsky, Moscow (RU); Niko Jarmo Juhani Meltola, Piispanristi (FI); Aleksi Elias Soini, Lieto (FI)

(73) Assignee: Arctic Diagnostics Oy, Turku (FI)

( * ) Notice: Subject to any disclaimer, the term of this patent is extended or adjusted under 35 U.S.C. 154(b) by 0 days.

(21) Appl. No.: 09/807,866

(22) Filed: Apr. 20, 2001

(30) Foreign Application Priority Data

Nov. 9, 1998 (FI) .................................................. 982422

(51) Int. Cl.$^7$ ........................ G01N 1/30; G01N 33/533; G01N 33/567; C07F 15/00
(52) U.S. Cl. ........................ 435/40.5; 424/9.61; 435/6; 435/40.51; 435/40.52; 436/546; 436/800; 530/391.3; 530/391.5; 530/402; 556/136; 987/3
(58) Field of Search ................................ 436/544, 546, 436/800

(56) References Cited

FOREIGN PATENT DOCUMENTS

| DE | 38 27 940 | 3/1990 |
|---|---|---|
| EP | 0705897 | 4/1996 |
| EP | 0811626 | 12/1997 |
| WO | WO 98/03865 | 1/1998 |

OTHER PUBLICATIONS

Kabakoff, Enzyme–immunoassay, CRC Press, Inc., 1980, Chapter 4, I. Maggio, editor.*
Fedorova et al., "Palladium (II)–coproporphyrin I as a Photoactivable Group in Sequence–specific Modification of Nucleic Acids by Oligonucleotide Derivatives," 259 *FEBS Letters* 335 (1990).
de Haas et al., "Phosphorescent Platinum/Palladium Coproporphyrins for Time–resolved Luminescence Microscopy", 47 *J. Histochemistry & Cytochemistry* 183 (Feb. 1999).
Ponamoreva et al., "Synthesis of Phosphorescent Metalloporphyrins With Isothiocyanate Groups", 21 *Russian J. Bioorganic Chem.* 296 (1995).
Mironov, Synthesis and Properties of New Chlorin and Bacteriochlorin Photosensitizers, 2625 *Soc'y Photo–optical Instrumental Engineers* 23 (1989).

* cited by examiner

Primary Examiner—Mary E. Ceperley
(74) Attorney, Agent, or Firm—James C. Lydon

(57) ABSTRACT

The preparation of phosphorescent metalloporphyrin labelling reagents and their use for preparation of phosphorescent conjugates with biomolecules. The labelling reagents obtainable are water soluble monofunctional derivatives of Pt- and Pd-coproporphyrins, where the term "monofunctional" refers to the number of reactive groups in the porphyrin moiety.

13 Claims, No Drawings

PORPHYRIN COMPOUNDS, THEIR CONJUGATES AND ASSAY METHODS BASED ON THE USE OF SAID CONJUGATES

This application is a U.S. national stage of International Application PCT/FI99/00898, filed Oct. 27, 1999 and published on May 18, 2000 in the English language.

FIELD OF THE INVENTION

This invention relates to the chemistry and applications of the metalloporphyrin. In particular it is related to novel photoluminescent metalloporphyrin compounds, their preparation and to the use of the said compounds as labelling reagents for biologically active molecules. This invention can be applied for example, in biomedical research and in-vitro diagnostics, in food industry, in chemical and pharmaceutical industry, in biotechnology as well as in environmental monitoring.

BACKGROUND OF THE INVENTION

Many (bio)analytical systems utilise certain chemical compounds and species as sensitive and specific probes for the determination of specific analytes and parameters. In particular, photoluminescent dyes are frequently used for labelling of biomolecules in different analytical applications. Various photoluminescent dyes with different physical, chemical and spectral properties have been described, that suit a wide range of applications, such as staining of proteins, nucleic acids, cells, for use in microscopy, immunoassays and DNA hybridisation assays. The most common families of the dyes include fluoresceins, rhodamines, coumarines, cyanines and BODIPY dyes (=boron dipyrrylmethine dyes). Families of the dyes which enable high detection sensitivity include photoluminescent lanthanide chelates and phosphorescent metalloporphyrins. A large number of photoluminescent fluorescent dyes and their biomolecule conjugates, such as protein conjugates and nucleic acid conjugates, have been developed in recent years. Many photoluminescent dyes as well as the corresponding labelling reagents and biomolecule conjugates are available commercially (see for example R. P. Haugland. Handbook of fluorescent probes and research chemicals, 6$^{th}$ Edn., Molecular Probes Inc., 1996) and widely used for diagnostics and research purposes. Photoluminescent conjugates of biomolecules are usually prepared by contacting a native biomolecule or a derivative of the biomolecule with a reactive derivative of a photoluminescent dye, also called labelling reagent. Examples of reactive groups in common labelling reagents include reactive esters (for example succinimidyl ester, sulphosuccinimidyl esters), isothiocyanato, chlorosulphonato, dichlorotriazinyl and maleimidyl groups. They enable simple and selective labelling of biomolecules via certain functional groups, most commonly via primary amino, thiol or hydroxy groups. Labelling can be performed under mild conditions and without using additional reagents. The availability of such standard labelling reagents and the corresponding photoluminescent bioconjugates is a requirement for development of analytical and diagnostic methods and applications. In many cases it is desirable to covalently attach the dye molecule via a spacer arm (usually 2–20 atoms long), in order to minimise the photochemical and biochemical interactions between the label and the biomolecule.

For those applications where high detection sensitivity is required, such as immunoassays and nucleic acid hybridisation assays, probes with long Stokes' shift and well resolvable spectral characteristics are needed. Significant improvement of sensitivity, especially when working with complex biological samples, can be achieved by using long decay time photoluminescent dyes in combination with time-resolved photoluminescent detection. The time-resolved detection concept allows significant reduction of background interference from scattering and intrinsic fluorescence and consequently provides high signal-to-noise ratio (E. Soini et al. U.S. Pat. No 4,374,120, 1983).

Long decay time photoluminescent lanthanide chelates, in particular the complexes of Eu, Th, Sm, Dy have been suggested for use in sensitive time-resolved fluoroimmunoassays (for example U.S. Pat. No. 4,565,790, U.S. Pat. No. 5,346,996, U.S. Pat. No. 5,571,897). They are presently used in a commercial time-resolved fluoroimmunoassay system DELFIA® (trademark of EG&G-Wallac, Turku, Finland). p-isothiocyanatobenzyl-diethylenetriamine-N$^1$, N$^2$,N$^3$,N$^4$-tetraacetic acid chelated with Eu$^{3+}$ is now commercially available for labelling of biomolecules, such as proteins, antibodies and nucleic acids.

Fluorescent complexes of ruthenium(II), osmium (II), and some other metals were suggested recently for use as long decay time fluorescent labels, particularly for oxygen sensors and for sensitive fluorescence immunoassays (J. Lakowicz et al., U.S. Pat. No. 5,660,991). Succinimidyl derivatives of Ruthenium bis(2,2'-bipyridine) (2,2'bipyridine-4,4'-dicarboxylic acid) have been described as labelling reagents for electrochemiluminescence immunoassays (U.S. Pat. No. 5,310,687).

A number of photoluminescent porphyrin dyes have been suggested for labelling of biomolecules, particularly for immunoassays (Schmidt D. et al. U.S. Pat. No. 4,614,723; Hendrix J., U.S. Pat. No. 4,707,454; Hendrix J., U.S. Pat. No. 5,464,741; Savitskii A. P. et al., Doklady Akademii Nauk SSSR, 1987, vol. 293, p.744, Braman, J. WO 96/11937). These dyes exhibit intense absorption bands around 400 nm and moderate absorption bands between 500 and 600 nm. Free base porphyrins usually emit fluorescence in red range of visible spectrum, whereas their metal complexes, mainly platinum(II) and palladium(II) porphyrins, exhibit bright phosphorescence in the same wavelength range even at room temperature (D. Dolphin, The Porphyrins, 1978, New York, Academic Press, vol. 3). Such properties make the porphyrin dyes promising in fluorescent and phosphorescent probing of biomolecules and particularly in time-resolved phosphorescence bioaffinity assays. A number of porphyrins as well as certain related structures, mainly biogenic polycarboxy porphyrins and water-soluble derivatives of tetraphenylporphyrin, have been suggested for such applications.

Water-soluble coproporphyrin-I was suggested by Savitsky et al. (Doklady Akademii Nauk SSSR, 1987, vol. 293, p.744) as a label for fluoroimmunoassays. A palladium(II) complex of coproporphyrin-I has been used for phosphorescence labelling of antibodies (Doklady Akademii Nauk SSSR 1989, vol. 304, p. 1005). In similar way some other polycarboxy porphyrins, including coproporphyrin-III, zinc (II)-coproporphyrin-I, dimethoxydeuteroporphyrin IX, hematoporphyrin IX, platinum(II)-coproporphyrin I and III, have been used for labelling various proteins. With these dyes covalent binding to proteins was usually achieved by carbodiimide method with various modifications. In a two-step procedure the carboxy groups of the porphyrin were first activated by carbodiimide in aqueous solution or in organic media and then allowed to react with protein amino groups in slightly alkaline aqueous solution. A drawback of the methods where carbodiimides are used for activation of porphyrins having more than one carboxy group, is that a mixture of different products is formed as a result of the carbodiimide activation. The mixture comprises porphyrins having from 0 to n pieces of activated carboxy groups where n is the number of carboxy groups in the porphyrin before the activation. Multi-point activation of porphyrins often causes significant crosslinking and inactivation of biomolecules such as proteins when they react with such reagents.

An additional drawback of the carbodiimide chemistry is that it does not allow the active product to be isolated in pure form, but the product remains in form of undefined mixture. Furthermore, the active carbodiimide adduct is instable. It is sensitive to hydrolysis as well as to many other nucleophiles. Typically, the carbodiimide adducts react intramolecularly producing non-reactive N-acylurea. The chemical instability of the carbodiimide-activated porphyrin adducts makes their use difficult and unreliable. Also porphyrin-antibody conjugates prepared by carbodiimide mediated coupling has been found to exhibit poor storage stability (Martsev et al., J.Immunol. Methods, 1995, vol. 186, p.293). The use of tetrasuccinimidyl esters of coproporphyrins as labelling reagent did not provide significant improvement in performance or stability of the conjugates (Martsev et al., J.Immunol. Methods, 1995, vol. 186, p.293).

In U.S. Pat. No. 4,614,723 Schmidt et. al. introduced the use of porphyrins comprising several carboxy groups as label for immunoassays. The method of activation of porphyrins according to Schmidt's patent follows same carbodiimide chemistry as described above. G. Sagner and R. Haas (EP 0811626 A1) describe a preparation method for labelling reagents from water-soluble platinum(II) porphyrins: platinum coproporphyrin-I (PtCP) and platinum tetra-(p-carboxyphenyl) porphine (PtTCPP). However, in the patent publication as well as in two other publication by R Haas (J. Histochem. Cytochem., vol. 45, p.1279 (1997), J. Histochem. Cytochem, vol. 47,183–196 (1999)) the detailed chemical structures and respective systematic names of the label remain ambiguous. For example, the systematic name of a compound which they trivially call as 'platinum coproporphyrin', has been written as 'Pt-3,8,13,18-tetramethyl-21H,23H porphine-2,7,12,17-tetrapropionic acid'. It is evident to a skilled person in the art, that upon insertion of a metal cation to the porphyrin cavity, a substitution occurs where the two hydrogen atoms bound to the positions 21 and 23 in the free base porhyrins are replaced. Thus, in case the authors mean phosphorescent metallo porphyrin chelate, the systematic name for the product should be 'Platinum (II) complex of 2,7,12,17-tetramethyl-21H,23H-porphine-3,8,13,18-tetrapropionic acid'. In EP 0811626A1, Sagner et. al., the labelling reagent was prepared by applying carbodiimide chemistry as applied in several other publications referred to above. The specific teaching of this Sagner's patent publication is that the activation reaction of the hydrophilic carboxy porphyrin has been carried out in dry organic solvent where hydrolysis of the activated derivatives should not take place. Preparation of the active porphyrin derivative is carried out by treating carboxy group containing porphyrins with a mixture of carbodiimide, N-hydroxy benzothiazole (=HOBt) and N-hydroxy succinimide in organic solvent, usually dimethylformamide. The reactive product formed in this process was used as such, without any purification or isolation of the reactive species. Since in such an activation process a mixture of undefined and unstable products is formed, the isolation of a single reactive species in pure form is very difficult. An additional drawback of the method is that the multiple activated porphyrins formed in the process may cause crosslinking and subsequent inactivation of the bioactive molecules.

Overall, a general problem of the carbodiimide mediated conjugation, when applied to polycarboxy porphyrins, is the lack of selectivity (i.e. all carboxy groups are subject to activation). Another problem is the formation of a complex mixture of labile compounds at the very first chemical stage of the conjugation reaction. For such mixtures it is difficult to apply conventional separation methods, so as to isolate in a pure form individual monofunctional reactive derivative (s), which can be characterised and then used for labelling of biomolecules.

In U.S. Pat. No. 5464741, U.S. Pat. No. 4,707,454 and in EP 0071991 Hendrix describes the use of porphyrins as label. U.S. Pat. No. 5,464,741 deals with the use of palladium(II) octaethylporphine alpha-isothiocyanate as a phosphorescent label for immunoassays. This monofunctional reagent is highly hydrophobic and not water-soluble. Consequently, it has limited use in labelling of biomolecules. An additional drawback of the reagents described by Hendrix is that the reactive group is bound directly next to the porphyrin moiety without any spacer arm. As usual, the lack of spacer arm has a tendency to significantly reduce the performance of the label. Furthermore, the same confusion with structures and names as found in the patent of Sagner et al., is also present in Hendrix's patent. The chemical structures of the compounds of issue remain ambiguous. Since the compound presented by Hendrix are octaalkyl porphyrins, which are not dealt in this invention, the Hendrix's patent is out of the scope of this invention.

In U.S. Pat. No. 4,707,545 and EP 0071991 Hendrix describes the use of chlorophyll and porphyrin derivatives as labels for fluoroimmunoassay. The key point in these two patents is the utilisation of the characteristic long Stokes' shift of chlorophyll probes for improving the detection sensitivity of the assay. The coupling of the chlorophyll derivatives to an active assay reagent is carried out by means of in situ activation. No chlorophyll labelling reagent has been isolated. Since these two patents deal only with fluorescent markers, they are out of the scope of present invention.

Shoichet et. al. (Siberian Chem. J. 4, 32, 1991) describes the use of palladium (II) complex of 5-isothiocyanotobenzamino octaethylporphine for labelling of oligonucleotides. This monofunctional labelling reagent is highly hydrophobic and not water-soluble, and consequently has limited use in labelling of biomolecules.

Braman et. al. (WO 96/11937) describes use of tetraphenylporphyrins for labelling of nucleosides, nucleotides, oligonucleotides and polynuleotides. According to Braman's publication, the porphyrin moiety on the labelled compound is detected on the basis of a reaction product produced by a porphyrin catalysed oxidation reaction. Said oxidation reaction may result in the formation of light, i.e., a chemiluminescent reaction, or a coloured compound, i.e., a colorimetric reaction. Since the Braman's publication deals with tetraphenylporphyrins which are not dealt in the present invention, and since detection in Braman's publication is not based on phosphorescence as in the present invention but on colorimetry and chemiluminescent, is the Braman's publication out of the scope of the present invention.

SUMMARY OF THE INVENTION

The characteristic features of this invention are disclosed in the claims. The present invention describes novel phosphorescent metalloporphyrin compounds, their preparation and the use of said compounds as labelling reagents for preparation of phosphorescent conjugates with biomolecules. The labelling reagents obtainable according to this invention are preferably water soluble monofunctional derivatives of Pt- and Pd-coproporphyrins. The term 'monofunctional' indicates that one of the four originally equal carboxy containing side chains of coproporhyrin has been differentiated and can be selectively further reacted. This invention offers also a route for preparation of such labelling reagents as well as the key intermediate compounds in a pure form, in other words, in form of stable organic compounds having defined chemical structure and properties. The compounds can be used as labelling reagents for labelling of biomolecules like peptides, proteins, hormones, nucleic acids, for labelling of cells, tissue or other chemical species having at least one functional group suitable for labelling reaction. The labelling reaction takes place under mild and slightly alkaline condition and can be carried out by any skilled person in the art. This invention also describes preparation of various bioconjugates using said metalloporphyrins as labelling reagents and the properties and the use of the such bioconjugates. The invention also describes the use of such bioconjugates in high sensitivity bioaffinity assays based on time-resolved phosphorescence. The bioaffinity assay may be e.g. an immunoassay, nucleic acid hybridisation and it can be performed in solution or on a solid substrate and the sample can be analysed with a time-resolved fluorometer/phosphorimeter. The assay can also be microscopic investigation of an immunocytological or immunohistological specimen.

DESCRIPTION OF THE PREFERRED EMBODIMENTS

The chemistry in the field of the use of the labelling reagents according to this invention most often takes place in aqueous media. Consequently, an applicable label needs to be water soluble and preferably hydrophilic. However, the aromatic tetrapyrrole unit i.e. porphin found in all porphyrins is hydrophobic in nature and not water soluble. In order to make the porphin unit water soluble, it must be substituted with hydrophilic side groups. One of the most preferable groups for this purpose is the carboxy group. In this context the term 'carboxy group' means the chemical group that equals with the chemical formula —COOH, i.e. the group that corresponds to carboxylic acids. On the other hand, the term 'oxycarbonyl group' means the chemical group that equals with the chemical formula —COO—, i.e. the diyl component found in carboxy group as well as in alkoxycarbonyl groups. The carboxy group is anionic in nature and has a tendency to make otherwise hydrophobic species water soluble in neutral and alkaline pH. Therefore, the most promising porphyrin compounds for labelling of biomolecules are those having carboxy (or the corresponding carboxylate) functional groups as substituents on the porphin periphery. For example, coproporphyrins, which contains carboxy groups, are sufficiently water-soluble and can be used as a label in aqueous media. In context to this text the term coproporphyrin includes both free bases as well as metallocomplexes of coporphyrin I and/or II.

A basic requirement for a commercially valuable labelling reagent is the monofunctionality with respect to the number of chemically reactive groups in the labelling reagent. This feature enables conjugation with biomolecules even in high target molecule concentration and high reagent concentration without causing deleterious cross-linking. The use of high concentrations makes labelling process more reliable and produces a product with higher degree of label substitution.

A further requirement for a commercially valuable labelling reagent is that the method used for the preparation of said reagent must enable reasonably high synthetic yield. An additional requirement is that the method of preparation enables isolation of the labelling reagent in pure form, in other words, in the form of a stable organic compound having a defined chemical structure and defined properties.

To improve the label performance, it is desirable to have an additional spacer arm (usually 2 to 20 atoms long) between the reactive site and the chromophoric moiety of the reagent. The spacer arm can serve for example to reduce steric hindrance around the reactive site, to make the reactive site more mobile, and to reduce the physical interaction between the label and the biomolecule.

It can be seen that the phosphorescent porhyrin-based labelling reagents according to prior art, usually lack one or more of the preferred properties.

In present invention we describe novel phosphorescent Pd- and Pt-coproporphyrins which fulfil the preferred properties as discussed above and which can be used for facile labelling of biologically active molecules having one or more functional groups suitable for the conjugation reaction. General structures that are characteristic for the labelling reagents which essentially fulfil the above mentioned requirements, are shown in Scheme I (Structure I and Structure II). In these compounds M is palladium (II) or platinum (II), $R_1$ is —OH, or —O$^-$X$^+$ group where X is a cation, most usually alkali metal cations or ammonium cations and $R_2$ is a chemical moiety bearing a linker unit —Y— and a functional group —Z where said functional —Z group can be used for selective covalent linkage to other molecules, such as biomolecules, and/or for further chemical modifications. The linker unit —Y— is either a covalent bond or a $C_1$–$C_{20}$ straight or branched alkylene, arylene, alkarylene or aralkylene group, which also may contain heteroatoms or heteroatoms containing side chains, or cyclic residues. The linker unit may also comprise or be composed of residues of polymers, preferably residues of hydrophilic polymers such as residues of polypeptides, polysaccharides, polynucleotides, polyethers or other. Among the most preferable chemical moieties —YZ are, according to this invention, those having a general formula —(CH$_2$)$_n$—Ph—Z, where —Z is either amino (—NH$_2$) or isothiocyanato (—NCS) group, —Ph— is a phenylene group, and n is an integer from 1 to 10.

From the Structure I and Structure II (Scheme I) one can see that the main object of this invention is the differentiation and subsequent functionalisation of one single oxycarbonyl group in coproporphyrins used as starting material. Such differentiation is realised via selective hydrolysis of the appropriate tetraalkyl esters of corresponding coproporphyrins, by using simple chemical procedure and technique.

Although it is clear that simple hydrolysis of tetraesters of coproporphyrins (as well as other polyesters of porphyrins) usually results in number of products, the present invention demonstrates that, if the hydrolysis reaction is carried out under the particular conditions described in this invention, surprisingly high amount of the coproporphyrin monoacid can be produced. After a simple chromatographic separation, a pure monocarboxy product can be isolated, whereas all the other by-products can be pooled and then transformed back into the form of tetraester by simple reesterification. Such reesterification reaction usually proceeds smoothly and almost quantitatively, thus saving most of the raw material which then can be recycled. Considering easy and simple recycling, the net yield of target monoacid of coproporphyrin may approach its theoretical limit.

The monoacid of coproporphyrin is the key compound for further monofunctionalisation and preparation of labelling reagents and bioconjugates according to this invention. This compound obtained in a pure form can easily be modified into the form of appropriate monofunctionalised derivative (s), labelling reagent(s) or a precursor of a labelling reagent. The modification of the carboxylic acid residue in coproporphyrin monoacid can be performed easily by applying the conventional chemistry related to modification of carboxy groups. The carboxy group of coproporphyrin monoacid can be modified, so as to introduce various functional groups via this site using a variety of available chemical methods.

According to this invention, the preferred methods of monofunctionalisation of the monoacid of coproporphyrins include, for example, activation of the carboxy group for subsequent coupling reactions using methods that involve succinimide esters, sulfosuccinimide esters, pentafluorophenyl esters, 4-nitrophenol esters, N-hydroxy benzotriazole esters, carbodiimide adducts and others.

If further lengthening is desirable, an additional spacer may be attached to the differentiated side chain. This can be carried out by using appropriate compounds such as heterobifunctional linkers. The preferable heterobifunctional compounds according to this invention include, for example, those in which the two functional groups are an aliphatic primary amino group and an aromatic primary amino group. This class of linker compounds is particularly preferred in the scope of this invention because of following reasons. First, due to the remarkable difference in reactivities between the two amino groups, the coupling with an active ester proceeds without a risk of deleterious crosslinking. Second, said class of linkers compounds comprise an inherent precursor for the reactive isothiocyanato group. However, the scope of this invention is not limited to the use of said class of linker compounds, but any of linker compounds, such as homobifunctional linker compounds and polyfunctional linker compounds can also be applied.

The next step in the synthetic scheme of a coproporphyrin labelling reagent is the transformation of relatively hydrophobic triester of the monofunctionalised coproporphyrin into a water-soluble form by alkaline hydrolysis of the remaining alkoxycarbonyl groups. As described above, the three carboxy substituents provide a structure with solubility in neutral and alkaline aqueous solutions. This stage is expected to preserve the introduced functional group, the spacer and the main structure of the coproporphyrin derivative from undesirable transformations. At this stage a water-soluble derivative of coproporphyrin is obtained which bears three carboxy groups and one differentiated side chain. The differentiated side chain that comprises a spacer unit and a reactive chemical group, such as amino or hydroxy, can be used for covalent coupling as such or after further chemical modification. For example, a coproporphyrin having an aromatic primary amino group, can be used for covalent coupling as such, or in the form of its conversion product isothiocyanate, which is obtained from said aromatic primary amino group by treatment with thiophosgene. Corresponding phenyl-isothiocyanato derivatives of phosphorescent Pt- and Pd-coproporphyrins are preferred target compounds and labelling reagents according to this invention. However, the scope of this invention is not limited to the use of isothiocyanato group as final reactive group, but other chemical groups can also be applied.

In certain cases, where covalent labelling of a target molecule in organic solvent is preferred, the non-water soluble form of a differentiated coproporhyrin, i.e. coproporphyrin comprising up to three alkoxycarbonyl groups, may also be applied as a labelling reagent. Scheme I (Structure I and Structure II) can also be used to illustrate the general structures of such compounds. In this case M is palladium (II) or platinum (II), $R_1$ is —OR group where R is $C_1$–$C_{20}$ straight or branched alkyl, aryl, alkaryl or aralkyl group, $R_2$ is a chemical moiety bearing a linker unit —Y— and a functional group —Z where said functional —Z group can be used for selective covalent linkage to other molecules, such as biomolecules, and/or for further chemical modifications. The linker unit —Y— is either a covalent bond or a $C_1$–$C_{20}$ straight or branched alkylene, arylene, alkarylene or aralkylene group, which also, may contain heteroatoms or heteroatoms containing sidechains or cyclic residues. The linker unit may also comprise or be composed of residues of polymers, preferably residues of hydrophilic polymers such as residues of polypeptides, polysaccharides, polynucleotides, polyethers or other. Among the most preferable chemical moieties —YZ are, according to this invention, those having a general formula —(CH$_2$)$_n$—Ph—Z, where —Z is either amino (—NH$_2$) or isothiocyanato (—NCS) group, —Ph— is a phenylene group, and n is an integer from 1 to 10.

The phosphorescent labelling reagents described above such as water-soluble phenyl-isothiocyanate derivatives of Pt- and Pd-coproporphyrins, can be used for facile labelling of various biomolecules such as peptides, proteins, haptens, nucleic acids; labelling of cells, tissue or other chemical species. As products of such labelling reactions the phosphorescent conjugates can be obtained, which are also the object of this invention. Said conjugates can be used as probes in sensitive bioaffinity assays, which are based on bioaffinity reactions and time-resolved phosphorescence detection.

The following non-limiting Examples are aimed to further demonstrate the invention. In the Examples below the compounds referred to (Compound 1 etc.) are disclosed in Schemes 2 to 8.

EXAMPLE 1

Synthesis of Coproporphyrin I Tetraisoamyl Ester (Compound 2)

A mixture of coproporphyrin I dihydrochloride (Compound 1, 300 mg, 412 µmol, prepared according to Smith et al., J.Chem. Soc. Perkin Trans I, 1471–1475 (1972)), 10 mL of isoamylalcohol and 0.5 mL of concentrated sulfuric acid was stirred at room temperature for 72 h. Then 1 mL of triethylamine was added, and the mixture was evaporated to dryness under reduced pressure at 100° C. The residue was washed with water and the organic phase was dried by filtration through anhydrous sodium sulphate to give 351 mg (91%) of the corresponding tetraester (Compound 2)

EXAMPLE 2

Synthesis of Coproporphyrin I Tetraethyl Ester (Compound 3)

To a mixture of of coproporhyrin I dihydrochloride (Compound 1, 300 mg, 412 µmol) and 50 mL of absolute ethanol, 2.5 mL of concentrated sulfuric acid was added and the mixture was stirred for 48 h at room temperature. Then 25% aqueous solution of ammonia was added until pH 4. The precipitate was filtered off, washed with 50 mL of water and dried under atmosphere. The product was crystallised from methylene chloride/methanol and dried under atmosphere to give 290 mg (92%) of Compound 3.

EXAMPLE 3

Synthesis of Coproporphyrin I Triethyl Ester (Compound 5)

To the mixture of Compound 3 (325 mg, 423 µmol) and 70 mL of tetrahydrofuran, 70 mL of 6 M hydrochloric acid was added and the reaction mixture was stirred for 10 minutes at room temperature. The reaction was stopped by addition of trisodium citrate (1 M, aq) until pH 4. The organic phase of the two phase system was diluted with 80 mL of chloroform, washed with water (50 mL), dried with anhydrous sodium sulphate (10 g) and evaporated to dryness. The products of hydrolysis were separated by column chromatography on silica gel using a stepwise gradient of methanol (0%–20%) in chloroform, as eluent. The first eluting compound was the recovered starting material (Compound 3), yield 104 mg (32%). The second eluting compound was the desired product Compound 5, yield 115 mg (37%).

EXAMPLE 4

Synthesis of Coproporphyrin II Triethyl Ester (Compound 7)

To the mixture of (390 mg, 509 µmol) of coproporphyrin II tetraethyl ester (Compound 6, prepared according to Clezy et al., Aust. J. Chem., 37, 143–154 (1984)) and 100 mL of tetrahydrofuran, 100 mL of hydrochloric acid (6 M, aq) was added and the reaction mixture was stirred for 10 minutes at room temperature. The reaction was stopped by addition of trisodium citrate (1 M, aq) until pH 4. The organic phase of the two phase system was diluted with 100 mL of chloroform, washed with water (50 mL), dried with anhydrous sodium sulphate and evaporated to dryness. The products of hydrolysis were separated by column chromatography on silica gel using a stepwise gradient of methanol (0%–20%) in chloroform, as eluent. The first eluting compound was the recovered starting material (Compound 6), yield 164 mg (42%). The second eluting compound was the desired product (Compound 7), yield 115 mg (31%).

EXAMPLE 5

Synthesis of Pd-Coproporphyrin II Triethyl Ester (Compound 8)

Mixture of 63 mg of $PdCl_2$ and 1 mL of N,N-dimethyl formamide (later DMF) was stirred for 5 minutes at 110° C. followed by decantation of the resulting brownish $PdCl_2$ solution. To the solid $PdCl_2$ residue an additional 1 mL portion of DMF was added and the solution was stirred at 110° C. for 5 minutes and decanted. The DMF treatment was repeated one more time and then all the three DMF fractions were combined. The DMF solution was heated to 110° C. and then added to hot DMF (5 mL) solution of Compound 7 (64 mg). The mixture was stirred at 110° C. until the characteristic absorption band for freebase CPII (Compound 7) at 620 nm disappears. Water (5 mL) was dropwise added to the hot reaction mixture and the precipitated product was filtered off. The precipitate was washed with water (5 mL), with ethanol (absolute, 5 ml) and dried under atmosphere. The product was dissolved in chloroform (20 mL) and filtered through a 2 cm thick layer of silica gel using CHCl3-MeOH, 9:1 v/v, as an additional eluent. The filtrate was concentrated under reduced pressure and the product was crystallised from chloroform/methanol. The crystalls were filtered off and dried under atmosphere to give 65 mg (90%) of Compound 8.

EXAMPLE 6

Synthesis of Pt-Coproporphyrin I Tetraethyl Ester (Compound 9)

To a solution of Compound 3 (300 mg, 391 µmol) in 10 mL of benzonitrile, $PtCl_2$, (600 mg, 2.26 mmol, 5.77 eq.) was added. The mixture was kept at 200° C. for 30 minutes. The cooled mixture was evaporated to dryness under reduced pressure at 150° C. The residue was purified by filtration through silica gel using chloroform as an eluent. The yield of Compound 9 was 286 mg (76%).

EXAMPLE 7

Synthesis of Coproporphyrin I Triisoamyl Ester (Compound 4)

To a stirred solution of Compound 2 (290 mg, 310 µmol) in 1,4-dioxane (50 mL), hydrochloric acid (50 mL, 6M, aq.) was added. The mixture was stirred at room temperature for 20 min, diluted with chloroform (100 mL), washed with water, aqueous ammonia, dried with anhydrous sodium sulphate and evaporated to dryness under reduced pressure at 40° C. The residue was purified by column chromatography on silica gel with chloroform-methanol (30:1) to give 120 mg (41%) of starting Compound 2 and 132 mg (49%) of mono acid derivative, Compound 4.

EXAMPLE 8

Synthesis of Pd-Coproporphyrin I Triisoamyl Ester (Compound 10)

Compound 4 (132 mg, 49%) was dissolved in of N,N-dimethylformamide (5 mL), heated to 100° C. and a solution of $PdCl_2$ (130 mg, 733 µmol) in of of N,N-dimethylformamide (2 mL) was added. The mixture was kept at 100° C. for 20 min. To the cooled mixture 0.2 mL of water was added. The precipitate was filtered off, washed with water and dried under atmosphere. The product was purified by filtration through silica gel with chloroform-methanol (20:1) as an eluent to give 135 mg (91%) of Compound 10.

EXAMPLE 9

Synthesis of Compound 11, Pt-Coproporphyrin I Triethyl Ester

To a refluxing solution of Compound 9 (220 mg, 229 µmol) in 1,4-dioxane (70 mL), hydrochloric acid (2.1 mL, 6M, aq.) was added. The mixture was refluxed for 20 min, cooled, diluted with chloroform (100 mL), washed with water, aqueous ammonia, and evaporated to dryness under reduced pressure. The residue was purified by column chromatography on silica gel using chloroform-methanol (30:1) as an eluent to give 110 mg (50%) of starting material (Compound 9) and 75 mg (35%) of the mono acid derivative (Compound 11).

EXAMPLE 10

Synthesis of Compound 13, a Derivative of Pt-Coproporphyrin I Triethyl Ester Having 2-(4-Aminophenyl)ethylamino Side Chain Compound 11 (75 mg, 80.5 µmol) was dissolved in methylene chloride (7 mL), and triethylamine (0.2 mL, 1.42 mmol) was added followed by addition of pentafluorophenyl trifluoroacetate (30 µL, 175 µmol). The mixture was stirred at room temperature for 10 min (Compound 12 formation) and 2-(4-aminophenyl)ethylamine (25 mg, 184 µmol) was added. The mixture was stirred at room temperature for 10 min, diluted with chloroform (20 mL), washed with water, hydrochloric acid (1M, aq.), water, sodium bicarbonate (saturated aqueous solution), dried with anhydrous sodium sulphate and evaporated to dryness under reduced pressure. The residue was purified by column chromatography on silica gel using chloroform-methanol (30:1) as an eluent to give 63 mg (75%) of Compound 13. $^1$H-NMR (CDCl$_3$, 400 MHz): 9.40, 9.39, 9.32 and 9.31 (s, 4H, meso-H), 6.19 and 5.93 (d, 4H, J=8.4 Hz, AB-system of Ph), 5.31 (t, 1H, J=5.6 Hz, COCH$_2$), 4.22–4.15 (m, 6H, COOC$\underline{H}_2$CH$_3$), 4.02 (m, 8H, CH$_2$CH$_2$COOR(3) and CH$_2$CH$_2$CONH), 3.31, 3.263, 3.26 and 3.25 (s, 12H, peripheral CH$_3$), 3.17 (m, 2H, CONHCH$_2$CH$_2$PhNH$_2$), 3.05 (m, 6H, CH$_2$CH$_2$COOR), 2.83 (t, 2H, J=7.1 Hz, CH$_2$CH$_2$CONH), 2.08 (t, 2H, J=6.8 Hz, CONHCH$_2$CH$_2$PhNH$_2$), 1.20 (m, 6 H, COOCH$_2$CH$_3$).

EXAMPLE 11

Synthesis of Compound 15, a Derivative of Pd-Coproporphyrin I Triisoamyl Ester Having 2-(4-Aminophenyl)ethylamino Side Chain To a stirred solution of Compound 10 (210 mg, 216.6 µmol) and triethylamine (0.3 mL, 2.13 mmol) in methylene chloride (15 mL), pentafluorophenyl trifluoroacetate (60 μL, 349 μmol) was added. The mixture was stirred at room temperature for 10 min (formation of Compound 14), and 2-(4-aminophenyl)ethylamine (48 mg, 350 μmol) was added. The mixture was stirred at room temperature for 10 min, diluted with chloroform (50 mL), washed with water, hydrochloric acid (1M, aq.), water, sodium bicarbonate (saturated aqueous solution), dried with anhydrous sodium sulphate and evaporated to dryness under reduced pressure. The product was purified by column chromatography on silica gel using chloroform-methanol (30:1) as an eluent to give 208 mg (88%) of Compound 15. $^1$H-NMR (CDCl$_3$, 400 MHz): 10.03, 10.01, and 10.00(2) (s, 4H, meso-H), 6.05 and 5.79 (d, 4H, AB-system of Ph), 5.08 (m, 1H, CONHCH$_2$), 4.33 (m, 8H, CH$_2$CH$_2$COOR(3) and CH$_2$CH$_2$CONH), 4.17 (t, 6H, J=6.8 Hz, COOCH$_2$CH$_2$—), 4.03 and 3.96 (m, 3 H, OCH$_2$CH$_2$CH(CH$_3$)$_2$), 3.60, 3.58(2), and 3.56 (s, 12H, peripheral CH$_3$), 3.22 (m, 8H, CH$_2$CH$_2$COOR(3) and CONHCH$_2$CH$_2$PhNH$_2$), 3.01 (t, 2H, J=7.1 Hz, CH$_2$CH$_2$CONH), 2.04 (t, 2H, J=6.8 Hz, CONHCH$_2$CH$_2$PhNH$_2$), 1.44 (m, 6H, OCH$_2$CH$_2$CH(CH$_3$)$_2$), 0.79 (m, 18H, OCH$_2$CH$_2$CH(CH$_3$)$_2$).

EXAMPLE 12

Synthesis of Compound 19, a Derivative of Pd-Coproporphyrin I Triethyl Ester Having 3-Aminopropylamino Side Chain To a stirred solution of Compound 16 (34.5 mg, 40.9 μmol) and triethylamine (41 mg, 409 μmol) in methylene chloride (2.5 mL) pentafluorophenyl trifluoroacetate (34.4 mg, 123 μmol) was added (formation of Compound 17). The solution was stirred for 60 minutes at room temperature and then mono-N-(tBOC)-propylenediamine (28.2 mg, 164 μmol) was added. The reaction mixture was stirred overnight at room temperature. Chloroform (10 mL) and sodium carbonate (10 mL, 1 M, aq.) were added and the mixture was stirred for 15 minutes. The organic phase was separated and washed with water (10 mL), citric acid (10 mL, 10% aq.) and finally with water (10 mL). The solution was dried with anhydrous sodium sulphate and evaporated to dryness and to give 33.5 mg (82%) of Compound 18. The product was dissolved in 6 mL of chloroform and 2 mL of trifluoroacetic acid was added.

The solution was stirred for 20 minutes at room temperature and evaporated to dryness under reduced pressure. The residue was dissolved in chloroform (10 mL) and washed with sodium carbonate (10 mL, 1 M, aq.) and water (10 mL). The solution was dried with anhydrous sodium sulphate and concentrated to 1 mL. The product was precipitated by dropwise addition of petroleum ether, filtered off and dried under atmosphere. Yield of Compound 19 was 27,0 mg (72%).

EXAMPLE 13

Synthesis of Compound 20, a Derivative of Pd-Coproporphyrin I Triethyl Ester Having 2-Aminoethylamino Side Chain A solution of Compound 17 (25 mg, 24.8 μmol) in methylene chloride (5 mL) was added to a solution of ethylenediamine (50 μL) in methylene chloride (10 mL). The mixture was stirred at room temperature for 30 min, washed with water (30 mL), dried with anhydrous sodium sulphate, and evaporated to dryness to give 20 mg (92%) of Compound 20.

EXAMPLE 14

Synthesis of Compound 22, a Derivative of Pd-Coproporphyrin II Triethyl Ester Having 2-(4-Aminophenyl)ethylamino Side Chain To a solution of Compound 8 (28.5 mg, 33,8 μmol) and triethylamine (20 μl, 144 μmol) in methylene chloride (5 mL), pentafluorophenyl trifluoracetate (40 μl, 142 μmol) was added. After stirring the solution for 15 minutes at room temperature 2-(4-aminophenyl)ethylamine (35 mg, 181 μmol) was added and the solution was stirred further for 1 h. The solution was diluted with methylene chloride (10 mL), washed with water (15 mL), hydrochloric acid (15 mL, 1 M, aq.), water (15 mL), sodium bicarbonate (15 ml, 1 M, aq.), dried with anhydrous sodium sulphate and evaporated to dryness. The product was crystallised from methylene chloride/methanol, fitrated off and dried under atmosphere to give 29,1 mg (90%) of Compound 22.

EXAMPLE 15

Synthesis of Compound 24, N-(2-(4-Aminophenyl) ethyl)-2-aminoethanamide

To a solution of tBoc-glycine (1.36 g, 7.77 mmol) and N-hydroxysuccinimide (894 mg, 7.77 mmol) in dioxane (3 mL), solution of dicyclohexyl carbodiimide (1.76 g, 8.47 mmol) in dioxane (3 mL) was added. After stirring the solution for 3 hours at room temperature the urea precipitate was filtrated off and the solution was evaporated to dryness. The product was crytallised from chloroform to give 950 mg (45%) of Compound 23a. Compound 23a (360 mg, 1,32 mmol) was dissolved in acetone and 2-(4-aminophenyl) ethylamine (216 mg, 1.58 mmol) was added. After stirring for 15 minutes at room temperature the solution was evaporated to dryness, dissolved in chloroform (10 mL), washed with water (2×15 ml), dried with anhydrous sodium sulphate and evaporated to dryness. The residue was further purified by column chromatography on silica gel using 0–20% methanol/chloroform as eluent: The yield of Compound 23b was 329 mg (85%). Compound 23b (329 mg, 1.12 mmol) was dissolved in chloroform (8 mL) and trifluoroacetic acid (4 mL) was added. After stirring for 30 minutes at room temperature the solution was evaporated to dryness. The residue was dissolved in water (6 mL) and the solution was made alkaline by addition of sodium hydroxide (6M, aq.) The aqueous solution was extracted with chloroform (6×30 mL). The chloroform fractions were combined and dried with anhydrous sodium sulphate. The solution was evaporated to dryness to give 175 mg (81%) of N-(2-(4-aminophenyl)ethyl)-2-aminoethanamide (Compound 24). Compound 25 (N-(2-(4-aminophenyl)ethyl)-2-aminopropanamide was prepared according to an analogous procedure as for N-(2-(4-aminophenyl)ethyl)-2-aminoethanamide.

EXAMPLE 16

Synthesis of Compound 26, a Derivative of Pd Coproporphyrin I Triethyl Ester Having a 2-(4-Aminophenyl)ethylcarbamylmethylamino Side Chain To a stirred solution of Compound 16 (71 mg, 84 μmol) and triethyl amine (84.8 mg, 840 μmol) in methylene chloride (5 mL), pentafluorophenyl trifluoroacetate (94.0 mg, 336 μmol) was added and the solution was stirred for 30 minutes at room temperature (formation of Compound 17). N-(2-(4-aminophenyl)ethyl)-2-aminoethanamide (Compound 24)(65 mg, 336 μmol) was added and the solution was stirred overnight at room temperature. The solution was diluted with methylene chloride (10 mL) and washed with sodium carbonate (10 mL, 1M, aq.), water (10 mL), citric acid (10 mL, 10%, aq.) and with water (10 mL). The solution was dried with anhydrous sodium sulphate, concentrated to volume of 2 ml and the product was precipitated by addition of hexane. The product was separated by centrifugation and dried under vacuum to give 65 mg (76%) of Compound 26.

EXAMPLE 17

Synthesis of Compound 27, a Derivative of Pd Coproporphyrin I Having a 2-(4-Aminophenyl) ethylcarbamylmethylamino Side Chain To refluxing solution Compound 26 (65 mg) in dioxane (5 mL), sodium hydroxide (200 µl, 6 M, aq.) was added. The solution was refluxed for 15 minutes, 5 mL of water was added and refluxing was continued for 30 minutes. The cooled solution was washed with chloroform and 10% solution of citric acid was added until pH 4. The precipitate was separated by centrifugation and the pellet was washed twice with water (resuspending and centrifuging) and evaporated to dryness twice from absolute EtOH. The product was further dried in desiccator over $P_2O_5$ to give 50 mg (84%) of Compound 27.

EXAMPLE 18

Synthetis of Compound 28, a Derivative of Pd-Coproporphyrin I Triethyl Ester Having 2-(4-Aminophenyl)ethylcarbamylethylamino Side Chain To a solution of Compound 16 (39.5 mg, 46,8 µmol) and triethyl amine (47.3 mg, 468 µmol) in methylene chloride (3 ml), a solution of pentafluorophenyl trifluoroacetate (59.0 mg, 211 µmol) was added (formation of Compound 17). Compound 25 (87.4 mg, 422 umol)(for preparation see EXAMPLE 13) in DMF (1 mL) was added to the reaction mixture and the mixture was stirred overnight at room temperature. The solution was diluted with chloroform (15 ml), washed with sodium carbonate (1 M, aq.), water (15 ml), citric acid (15 ml, 10%), water (15 ml) and dried with anhydrous sodium sulphate. The product was evaporated to dryness and purified by preparative TLC using 10% methanol-chloroform as an eluent to give 31.4 mg (65%) of Compound 28.

EXAMPLE 19

Synthesis of Compound 29, a Derivative of Pd-Coproporphyrin I Triethyl Ester Having a γ-(N-Maleimido)butylamidopropylamino Side Chain To a solution of Compound 19 (13.0 mg, 12.8 µmol) in chloroform (1 mL), triethylamine (12.9 mg, 128 µmol) and γ-(N-maleimido)butyroxy succinimide (7.2 mg, 25.6 µmol) were added and the solution was stirred overnight at room temperature. Sodium bicarbonate (1 ml, saturated aqueous solution) was added and the mixture was stirred for 1 h. The mixture was diluted with chloroform (5 mL) and the organic phase was washed two times with 10 mL of water, dried with sodium sulphate and evaporated to dryness. The residue was dissolved in methylene chloride (1 mL) and precipitated by dropwise addition of hexane. The precipitate was filtered off and dried under atmosphere. Yield of Compound 29 was 13.2 mg (97%).

EXAMPLE 20

Synthesis of Compound 30, a Derivative of Pd-Coproporphyrin I Having 2-Aminoethylamino Side Chain To a refluxing solution of Compound 20 (20 mg, 22.6 µmol) in dioxane (15 mL) sodium hydroxide (0.2 mL, 6M aq.) was added. The mixture was refluxed for 30 min, 15 mL of water was added, refluxed for additional 30 min, cooled, and washed with methylene chloride (30 mL). To the resulting aqueous phase hydrochloric acid (1M) was added until pH 4. The precipitate was separated by centrifugation, washed with water (2×10 mL), and dried at 40° C. under vacuum (~20 mmHg) to yield 17 mg (90%) of Compound 30.

EXAMPLE 21

Synthesis of Compound 31, a Derivative of Pd-Coproporphyrin I Having 3-Aminopropylamino Side Chain To a refluxing solution of Compound 19 (25 mg, 27.3 µmol) in dioxane (10 mL), sodium hydroxide (200 µl, 6 M, aq.) was added and refluxing was continued for 20 minutes. 10 mL of water was added and refluxing was continued for 30 minutes. The cooled solution was washed with chloroform (10 mL) and the product was precipitated by addition of hydrochloric acid (1 M) until pH 4. The precipitate was separated by centrifugation, washed with water (2×10 mL) and evaporated twice to dryness from absolute ethanol. The product was further dried in desiccator over silica gel to give 19 mg (80%) of Compound 31.

EXAMPLE 22

Synthesis of Compound 32, a Derivative of Pd-Coproporphyrin I Having 4-(N-Maleimidomethyl) cyclohexylcarboxamidoethylamino Side Chain To a stirred suspension of 12 mg (14.3 µmol) of Compound 30 in water (10 mL) sodium bicarbonate (40 mg) was added and clear solution was obtained after stirring at 40° C. for 10 min. The solution was diluted with dioxane (10 mL) and N-succinimidyl 4-(maleimidomethyl)cyclohexane carboxylate (20 mg) in dioxane (2 mL) was added. The mixture was stirred at room temperature for 12 h. The reaction mixture was washed with methylene chloride (30 mL), and hydrochloric acid (1M, aq.) was added until pH 4. The precipitate was separated by centrifugation, washed with water (2×10 mL), and dried at 40° C. in vacuum (~20 mm Hg) to yield 13 mg (90%) of Compound 32.

EXAMPLE 23

Synthesis of Compound 34, a Derivative of Pd-Coproporphyrin I Having 2-(4-Isothiocyanatophenyl)ethylamino Side Chain To a refluxing solution of Compound 21 (100 mg, 91.9 µmol) in dioxane (35 mL), sodium hydroxide (0.2 mL, 6M aq) was added. The mixture was refluxed for 30 min, water (20 mL) was added and the mixture was refluxed for additional 30 min. The reaction mixture was washed with chloroform (30 ml), and then chloroform (20 mL) and sodium bicarbonate (5 mL, saturated aqueous solution) were added. To the vigorously stirred mixture, thiophosgene (90 ul, 1.17 µmol) was added and the stirring was continued at room temperature for 30 min. The layers were separated and the aqueous phase was washed with chloroform. The product was precipitated by addition of hydrochloric acid (2M, aq.) until pH 4. The precipitate was separated by centrifugation, washed with water, and dried in vacuum desiccator over silica gel to yield 65 mg (77%) of Compound 34.

EXAMPLE 24

Synthesis of Compound 35, a Derivative of Pd-Coproporphyrin I Triethyl Ester Having 6-(1-O-Methyl)mannopyranosylamino Side Chain To a solution of Compound 17 (6 mg, 5.9 µmol) in methylene chloride (2 mL) a solution of 6-amino-2,3-O- isopropylidene-methyl α-D-mannopyranoside (10 mg) in 1 mL of pyridine was added. The mixture was stirred at room temperature for 30 minutes, washed with water (30 mL), dried with anhydrous sodium sulphate, and concentrated under reduced pressure. The product was purified by column chromatography on silica gel (20 mL) using diethyl ether-methylene chloride (10:90) as an eluent to give Compound 35, which was precipitated from methylene chloride (1 mL) by addition of hexane (5 mL). The precipitate was filtered off and dried at 40° C. under vacuum (~20 mmHg) to give 6 mg (89%) of Compound 35. $^1$H-NMR (CDCl$_3$, 300 MHz): 9.87, 9.85, 9.81 and 9.80 (s, 4H, meso-H), 5.85 (dd, 1H, J=3.9, 7.8 Hz, CONH), 4.15–4.35 (m, 14H, COOC$\underline{H}_2$CH$_3$, C$\underline{H}_2$CH$_2$COOR(3) and CH$_2$C$\underline{H}_2$CONH), 3.54, 3.53, 3.50 and 3.49 (s, 12H, peripheral CH$_3$), 3.20 (m, 8H, CH$_2$C$\underline{H}_2$COOR), 3.06 (s, 3H, OMe from sugar) 2.70 (m, 2H, NH C$\underline{H}_2$), 1.40 (s, 6 H, Me of acetonide), 1.20 (m, 9H, OCH$_2$C$\underline{H}_3$).

EXAMPLE 25

Synthesis of Compound 36, a Derivative of Pd-Coproporphyrin I Having 6-(1-O-Methyl) mannopyranosylamino Side Chain To a refluxing solution of Compound 35 (6 mg, 5.2 μmol) in dioxane (4 mL), hydrochloric acid (0.1 mL, 6M, aq.) was added. The mixture was refluxed for 10 min and 0.2 mL of 6M aqueous solution of sodium hydroxide was added. The mixture was refluxed for 30 min, 5 mL of water was added, the mixture was refluxed additional 30 min, cooled, and washed with methylene chloride (10 mL). To the resulting aqueous phase, hydrochloric acid (1M, aq.) was added until pH 4. The precipitate was separated by centrifugation, washed with water (2×10 mL), and dried at 40° C. under vacuum (~20 mmHg) to yield 4.5 mg (85%) of Compound 36.

EXAMPLE 26

Synthesis of Compound 38, a Derivative of Pt-Coproporphyrin I Having 2-(4-Isothiocyanatophenyl)ethylamino Side Chain To a refluxing solution of Compound 13 (57 mg, 54.3 μmol) in dioxane (20 mL), sodium hydroxide (0.2 mL, 6M, aq.) was added. The mixture was refluxed for 30 min, 10 mL of water was added, the mixture was refluxed for additional 30 min, cooled, and washed with chloroform. To the resulting aqueous solution of trisodium salt of Compound 37, chloroform (20 mL) and sodium bicarbonate (5 mL, saturated solution) were added followed by addition of thiophosgene (60 μL, 780 μmol). The mixture was vigorously stirred at room temperature for 30 min and the layers were separated. The aqueous phase was washed with chloroform, and the product was precipitated by addition of hydrochloric acid (2M, aq.) until pH 4. The precipitate was separated by centrifugation, washed with water, and dried in vacuum desiccator over silica gel to yield 23 mg (48%) of Compound 38.

EXAMPLE 27

Labelling of Rabbit Anti-mouse IgG with Compound 34

1 mg of Compound 34 was is dissolved in 0.5 mL of dimethylformamide and 0.05 mL of this solution was added to 1 mL of Rabbit anti-mouse-IgG antibody solution (1 mg/mL, 0.05 M carbonate buffer, pH 9.5). The mixture was incubated overnight at room temperature and then passed through a Sephadex G-25 column equilibrated with PBS buffer (phosphate 50 mM, NaCl 150 mM, pH 7,5). The fraction of the first peak which corresponds to the labelled protein was collected. Labelled IgG was characterised spectrophotometrically and then stored at +4° C. in presence of 1% BSA and 0.1% sodium azide, for further use.

EXAMPLE 28

Mouse IgG Immunoassay Using a Biologically Active Assay Reagent Labelled with Compound 38.

12-well microtiter strips (Nunc) were coated with polyclonal goat anti-mouse-IgG antibody. 0.2 mL of antibody solution (10 microgram/mL) in carbonate buffer, pH 9.6, were added to each well and incubated overnight at room temperature. To inhibit non-specific binding the strips were post-coated with PBS containing bovine serum albumine (bovine serum albumine 10 mg/mL, phosphate 50 mM, NaCl 150 mM, pH 7.5, 1 h, room temperature). The strips were washed with PBS containing 0.05% (w/w) of Tween-20 (PBST).

Serial dilutions of mouse IgG were made in PBST, 0.2 mL of each concentration was added to the wells of microtiter strip, incubated for 1 h at 37° C. and washed 4 times with PBST. Then 0.1 mL of anti-mouse-IgG antibody labelled with Compound 38 (1 microgram/mL) was added to each well, incubated for 1 h at 37° C. and then washed 4 times with PBST. The anti-mouse-IgG conjugate was prepared by analogous manner to Example 27 but using Compound 38 and Mouse IgG instead of 34 and Rabbit IgG.

A solution of 0.01 M KOH containing 3 mM cetyltrimethylammomium bromide was added to each well (0.2 mL) and incubated 15 min to desorb labelled antibodies from the solid phase. Then 0.02 mL of freshly prepared solution containing 50 mg/mL of Na$_2$SO$_3$, 60 mg/mL KH$_2$PO$_4$ was added into each well and time-resolved phosphorescence was counted using time-resolved fluorescent reader Arcus-1230 (trademark of Wallac Oy, Turku, Finland). The Arcus was equipped with 535 nm excitation and 650 nm emission filters which correspond to bands of the dye. The delay time was set to 0.05 ms, whereas the gate time was 0.2 ms. Measured signals were plotted as a function of concentration of mouse IgG (i.e. antigen) to obtain a calibration graph.

EXAMPLE 29

Immunocytochemical Staining of Human Colon Cancer Cells

Detection of cancer antigen C242 in isolated human colon cancer cell line (C205) was used as model for investigation the feasibility of Compound 34 for in-situ immunostaining. The cells were grown in plastic Petri dishes in RPMI-1640 culture medium for 24 hours at 38° C. For specific labelling, the cultured cells were rinsed once with PBS-BSA (0.1% bovine serum albumin and 0.9% NaCl in phosphate buffer, pH 7.4) and incubated with a monoclonal anti-human C242 antibody (Wallac, Turku, Finland) at a concentration of 10 μg/mL in PBS for 30 min at room temperature. The cells were then rinsed three times for 5 min with PBS-BSA. After removing the cells from the Petri dish by scraping, they were incubated with Rabbit anti mouse IgG labelled with Compound 34, at a concentration of 10 μg/mL for 30 minutes. The cells were rinsed with PBS, fixed with 3% glutaraldehyde (Fluka) in PBS for 10 min at room temperature and rinsed with PBS. The cells were dehydrated through increasing alcohol concentrations, cleared in xylene in a Coplin jar and mounted in Merckglas (trademark of Merck, Germany). Imaging was carried out using the Leitz Aristoplan fluorescence microscope equipped with appropriate excitation and emission filters for time-resolved fluorescence imaging as described by Sevéus et al. in Cytometry, 13 (1992) pp 329–338 and in WO 9410568.

Scheme 1
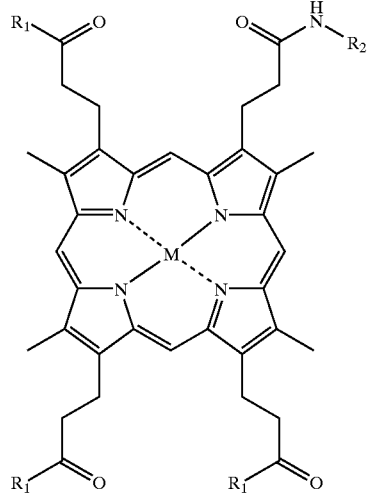
Structure I
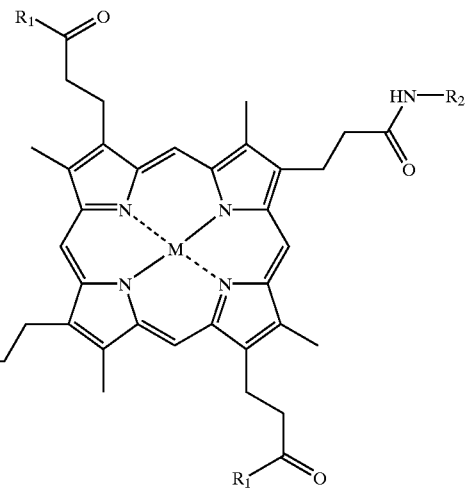
Structure II
Scheme 2
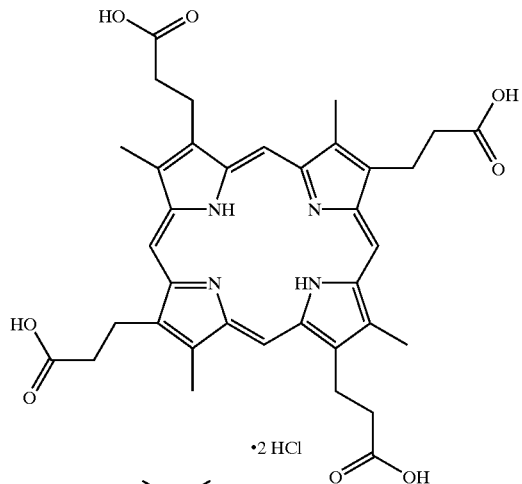
Compound 1
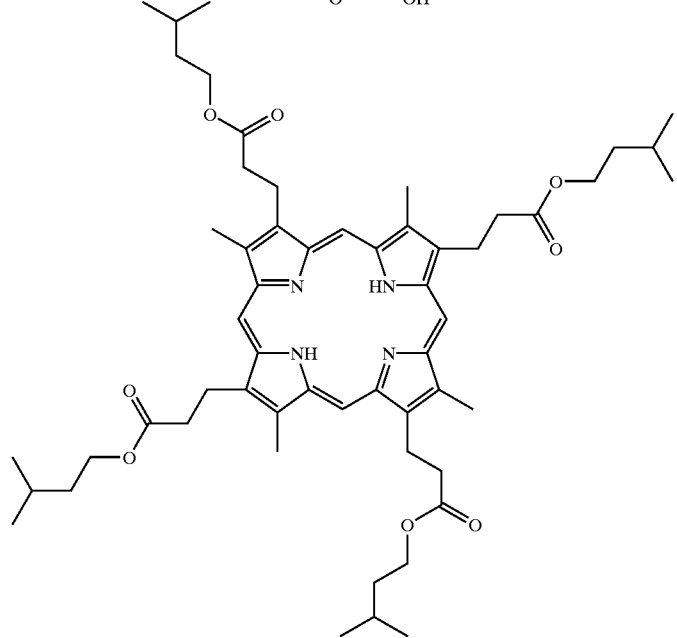
Compound 2

Compound 3
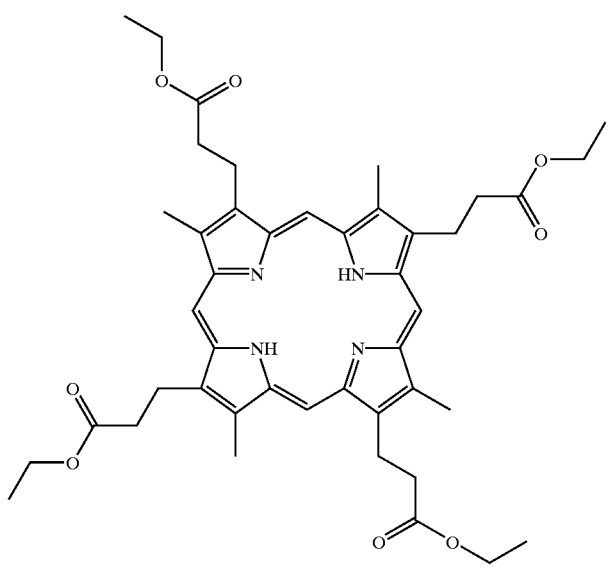
Compound 4
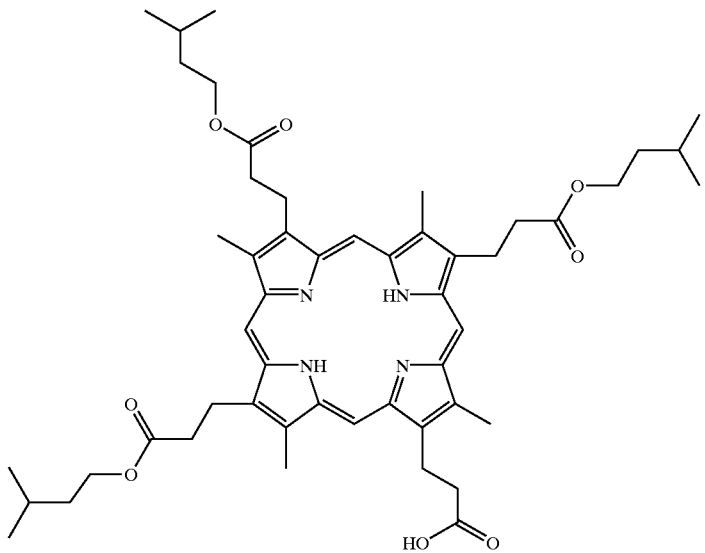
Compound 5
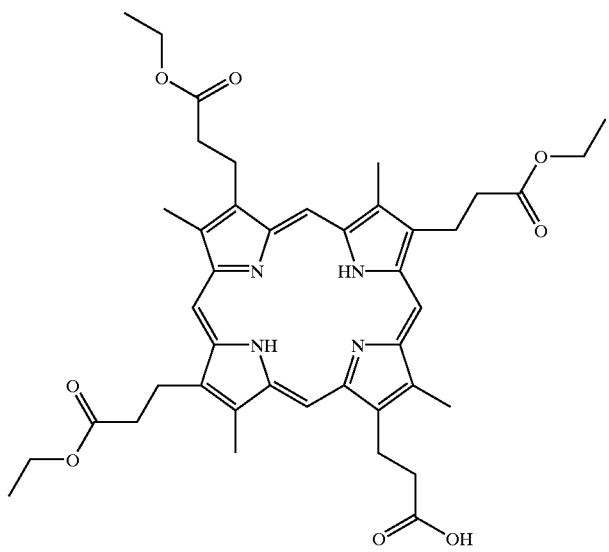

-continued
Compound 6
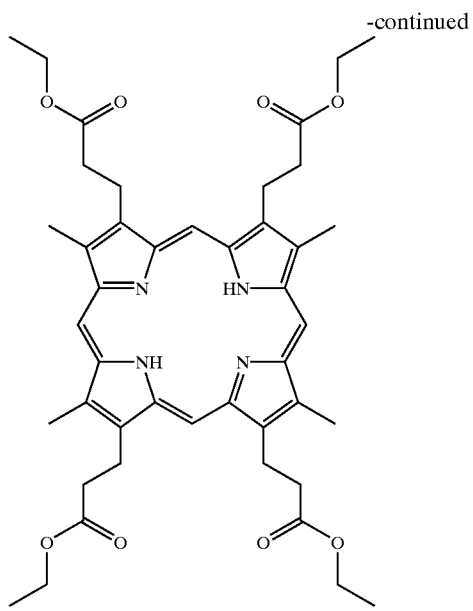
Scheme 3
Compound 7
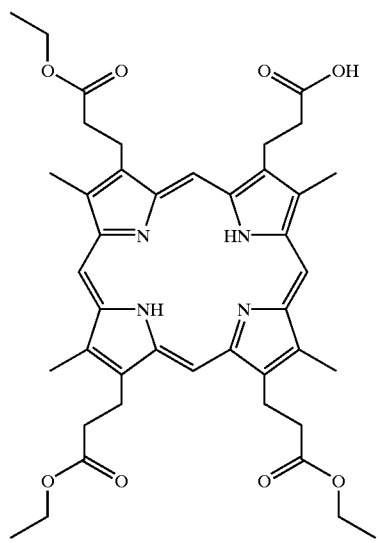
Compound 8
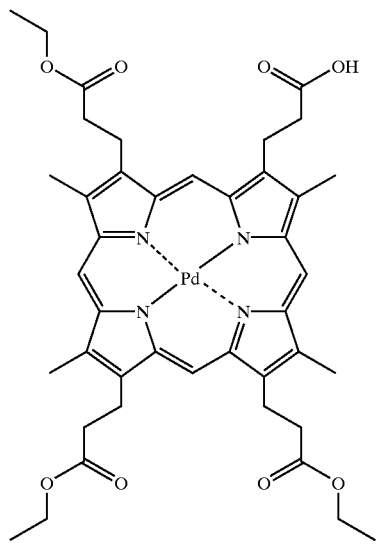

Compound 9
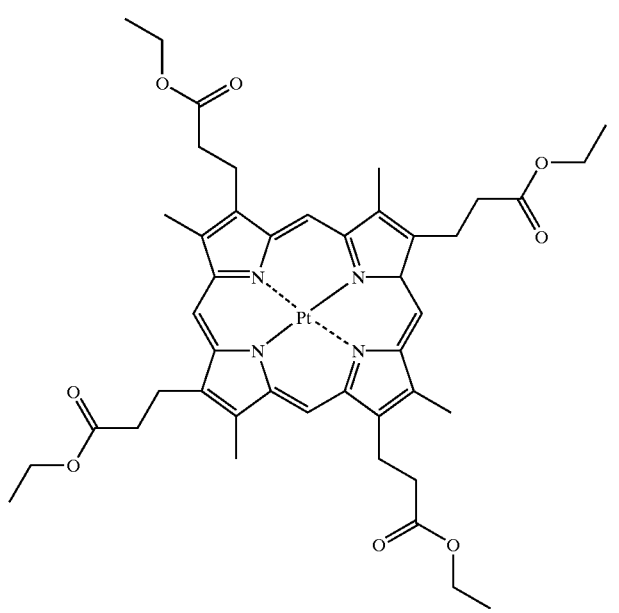
Compound 10
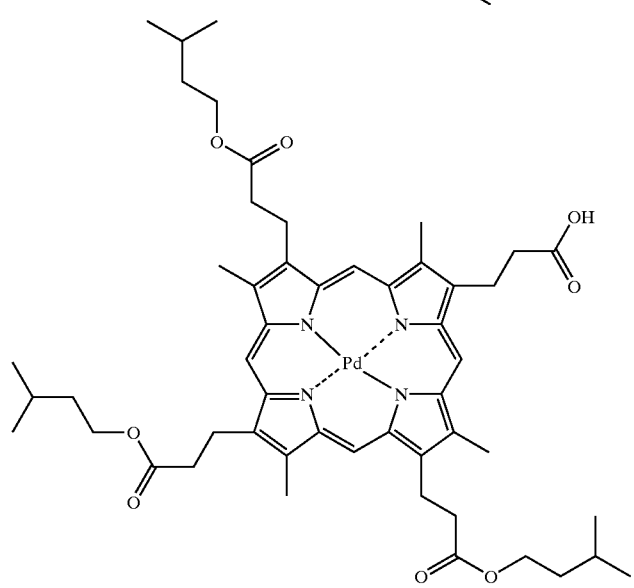
Compound 11
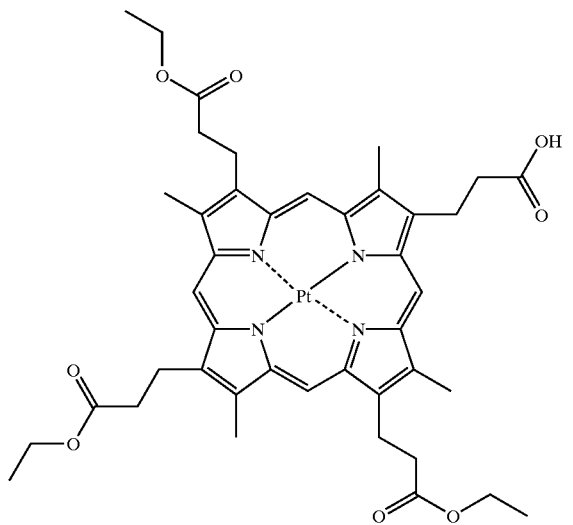

Compound 12
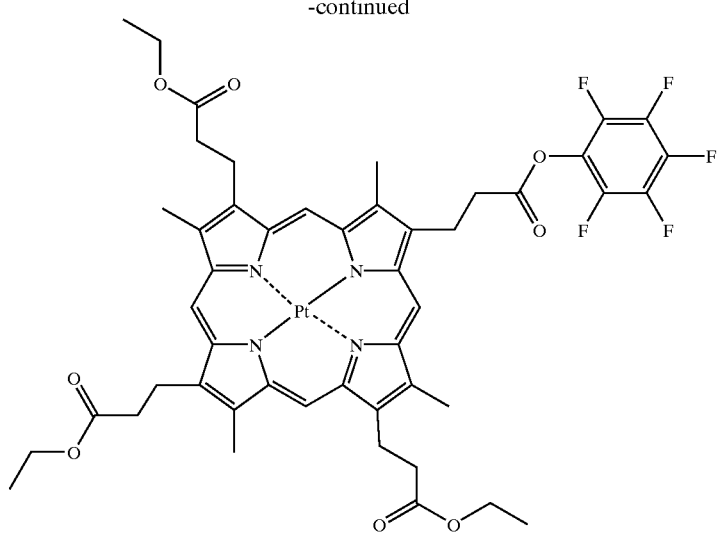
Scheme 4
Compound 13
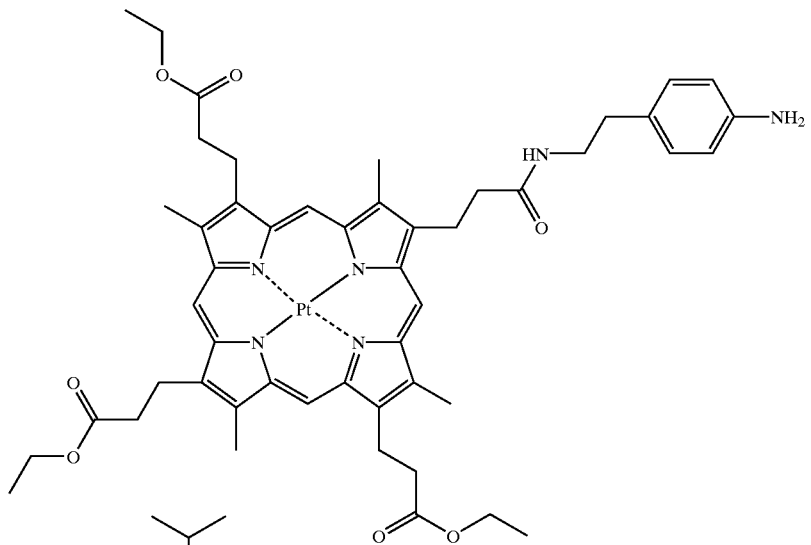
Compound 14
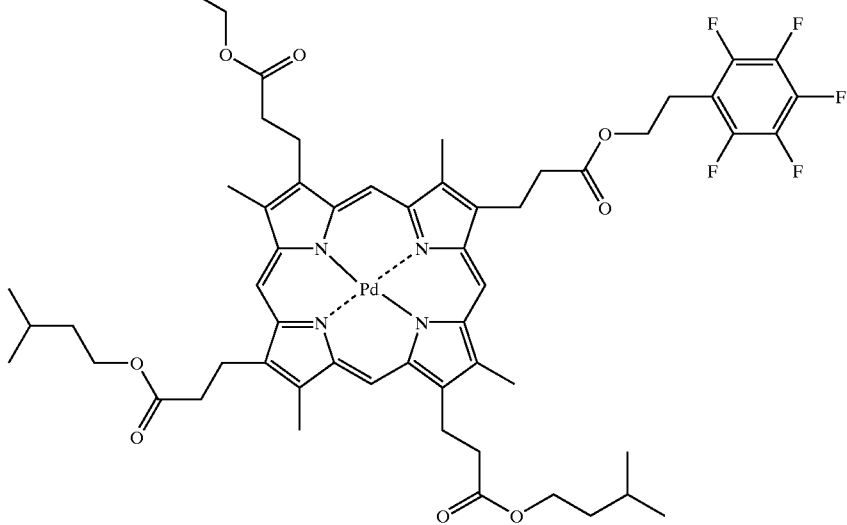

-continued
Compound 15
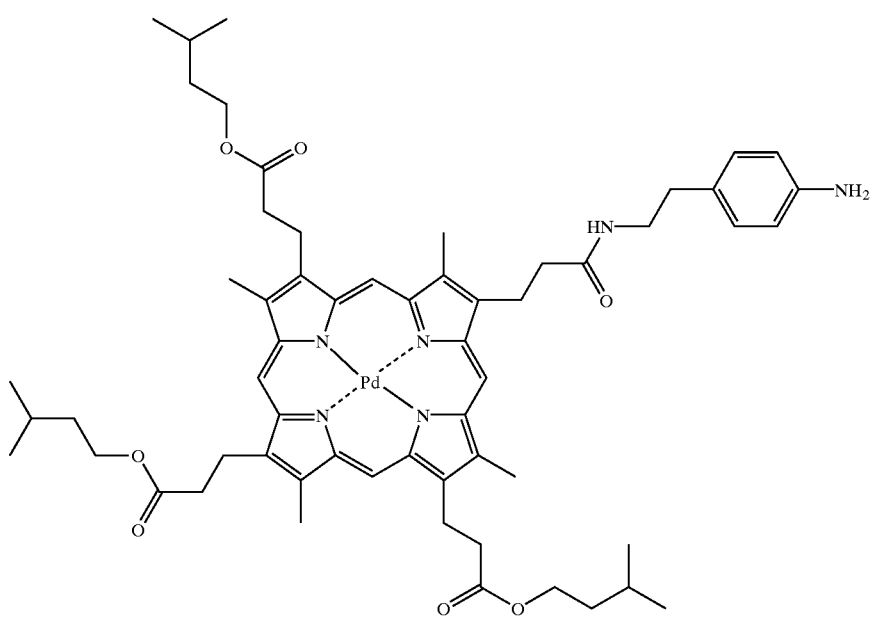
Compound 16
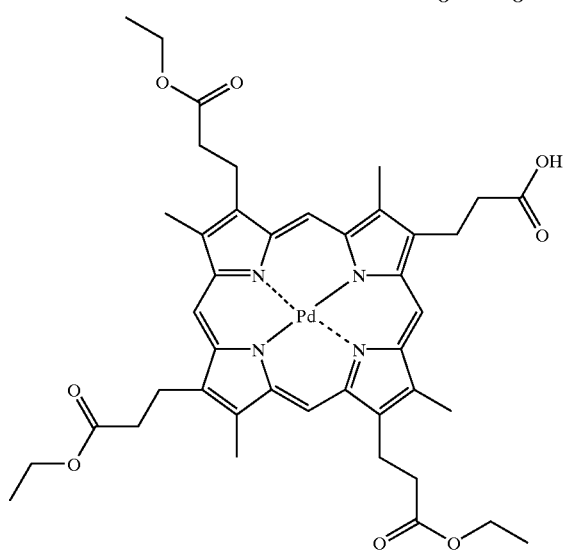
Compound 17
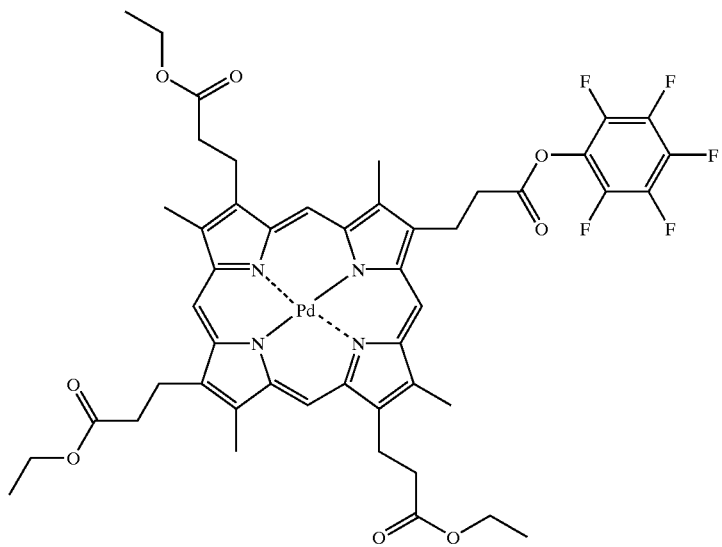

Compound 18
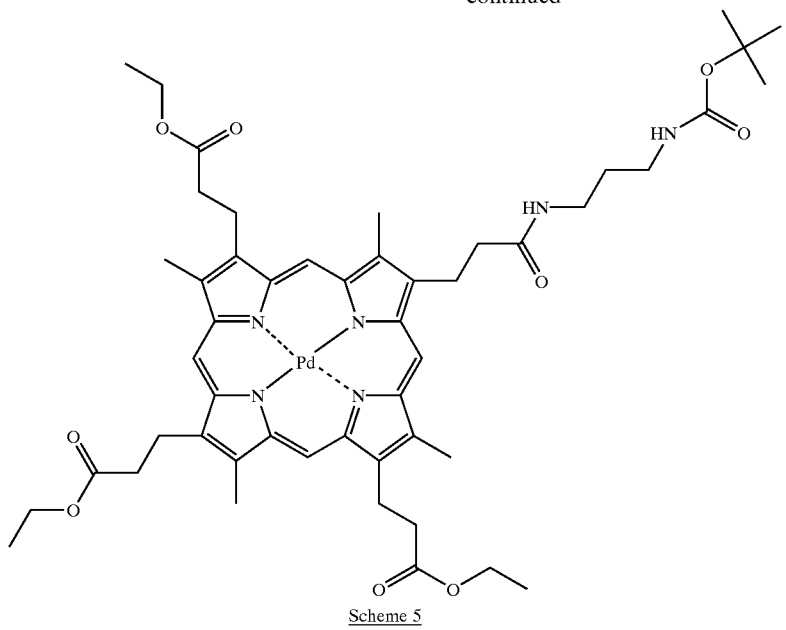
Scheme 5
Compound 19
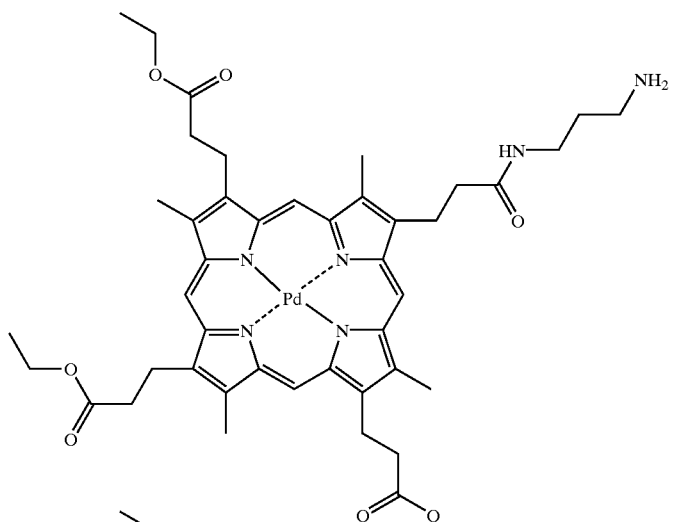
Compound 20
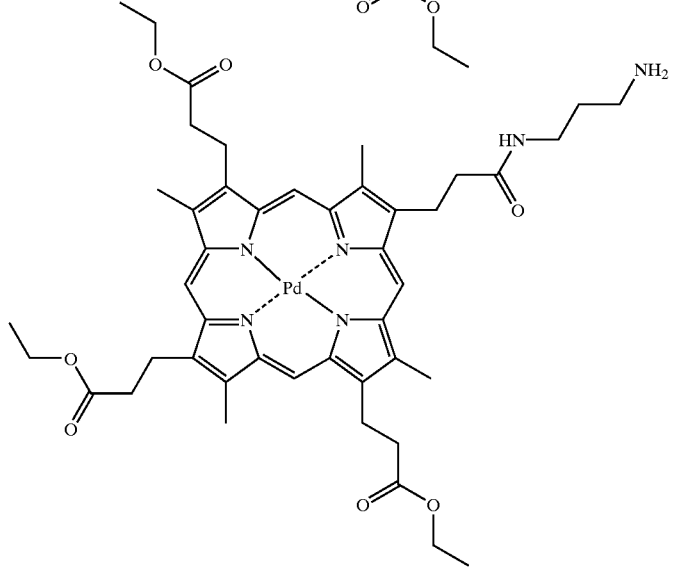

-continued
Compound 21
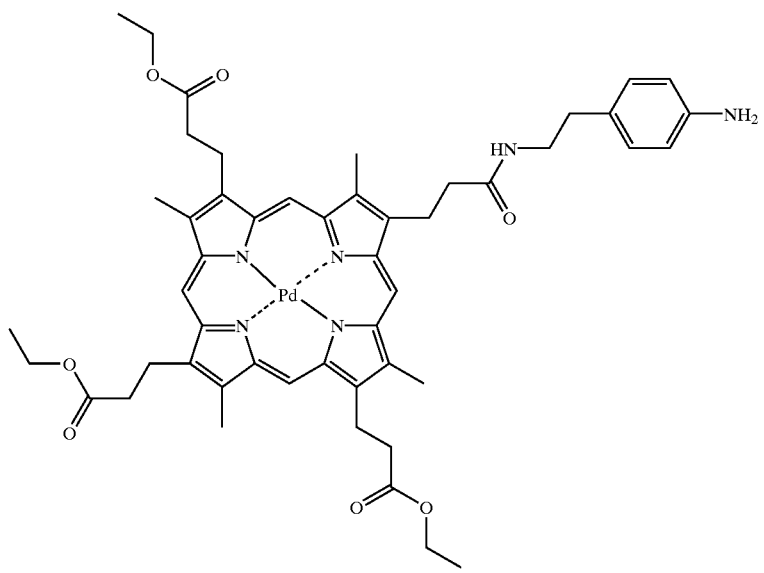
Compound 22
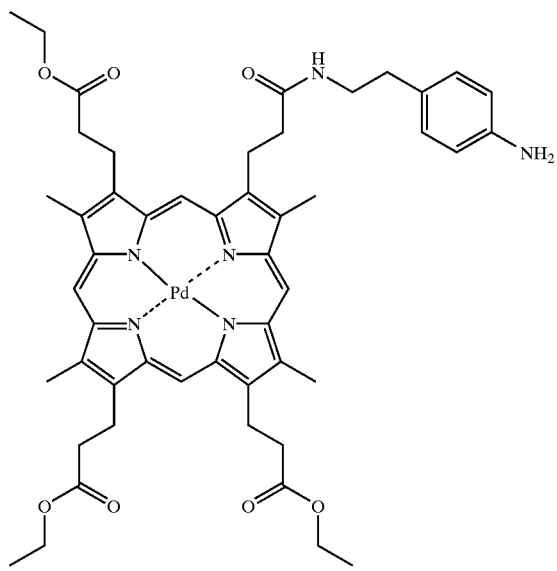
Compound 23a
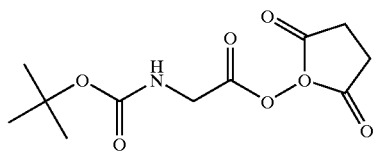
Compound 23b
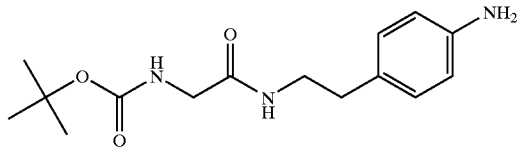
Compound 24
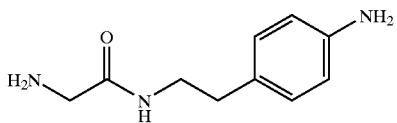

-continued
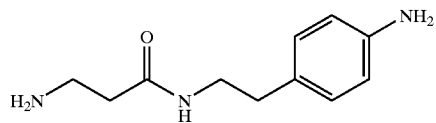
Compound 25
Scheme 6
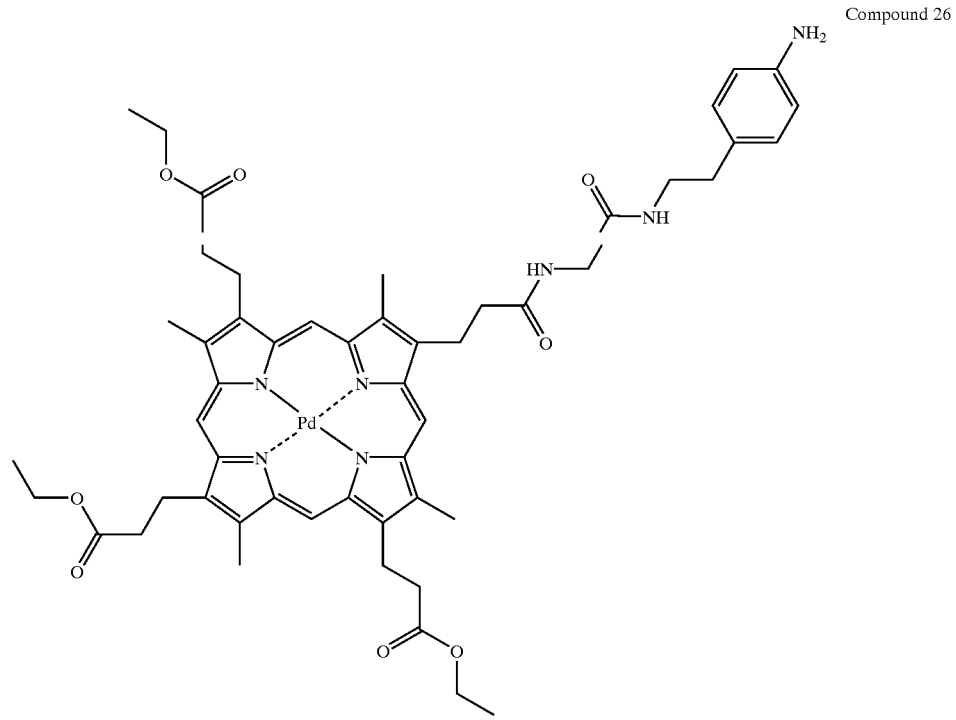
Compound 26
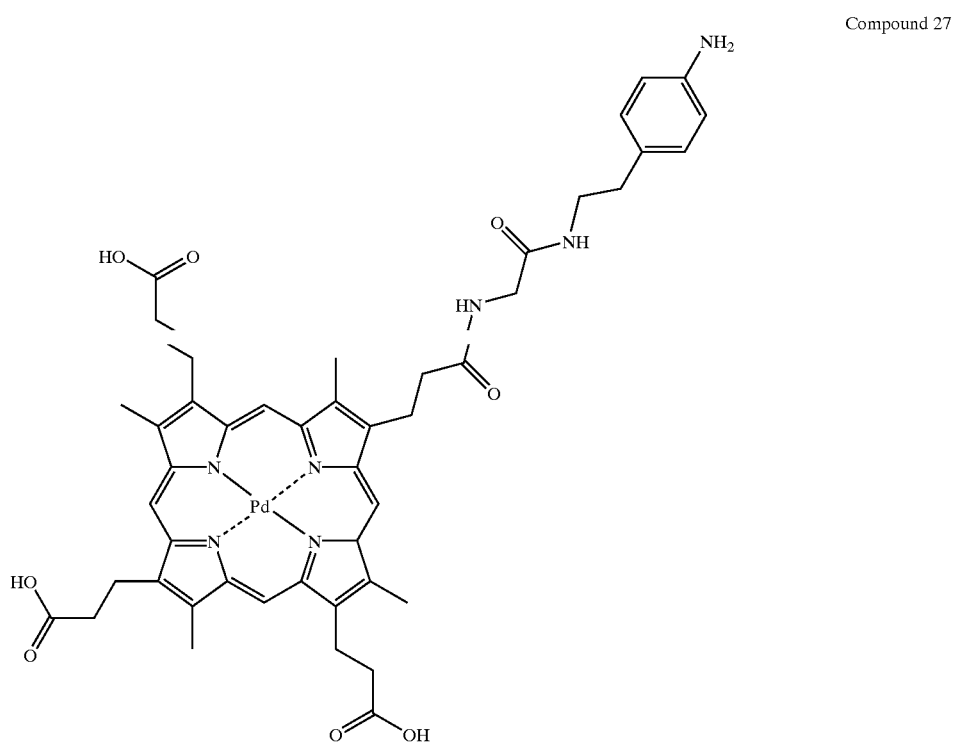
Compound 27

-continued
Compound 28
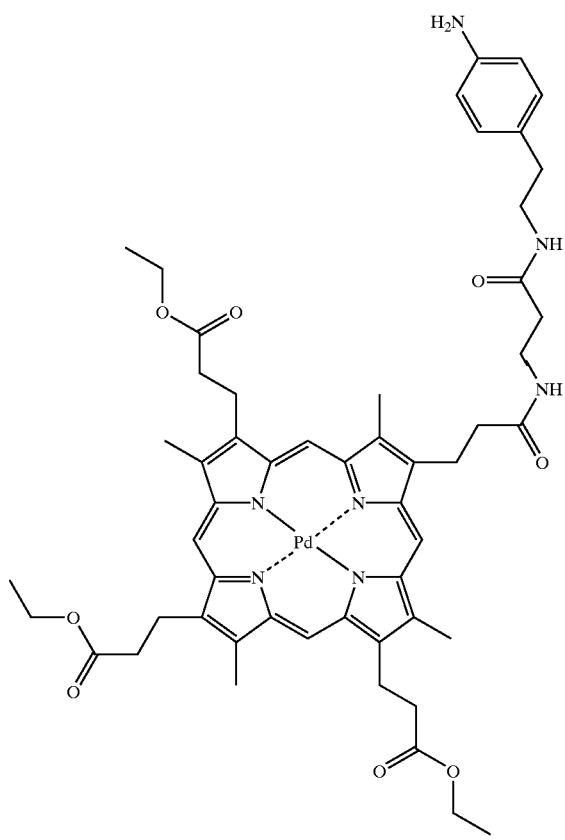
Compound 29
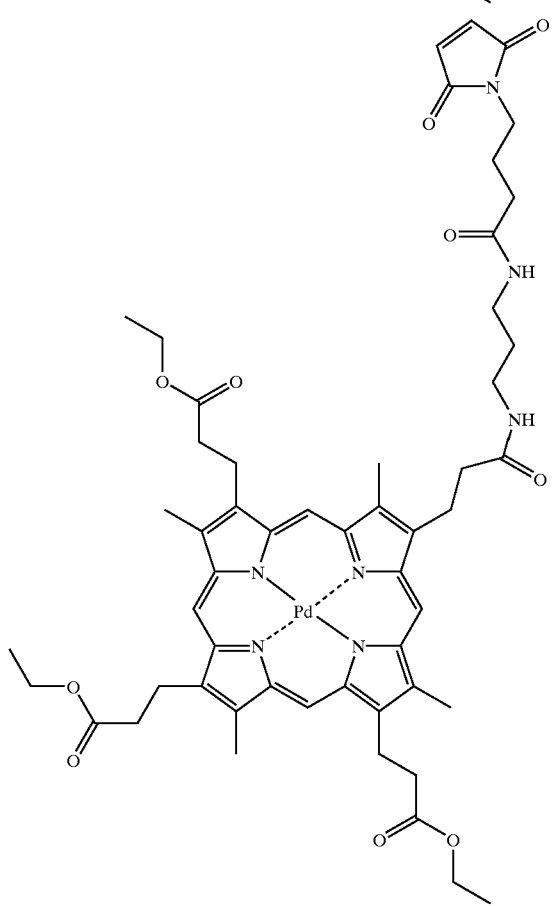

Scheme 7
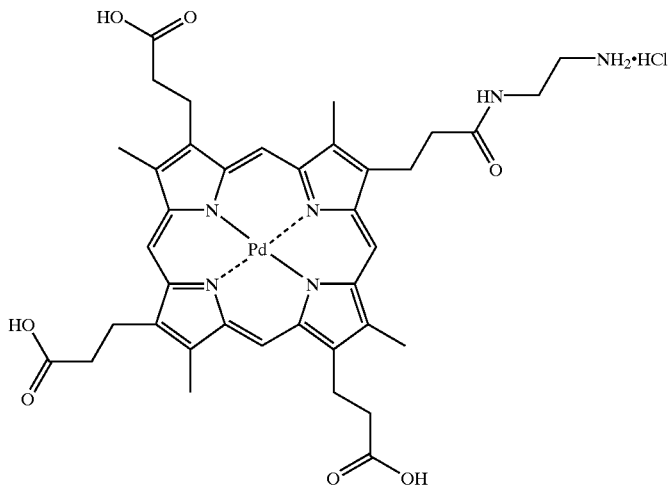
Compound 30
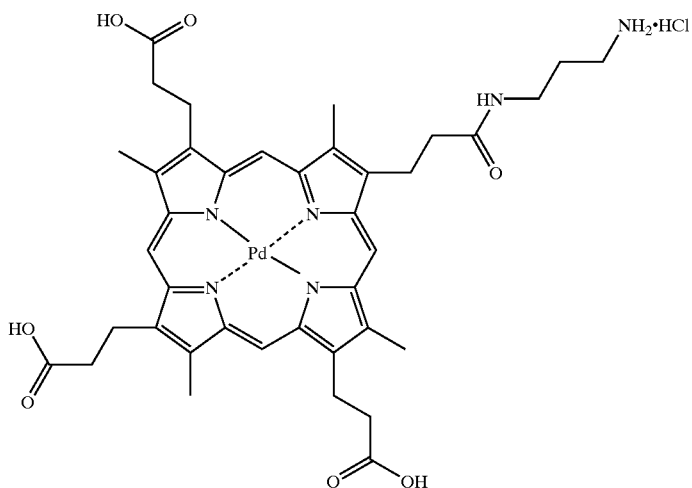
Compound 31
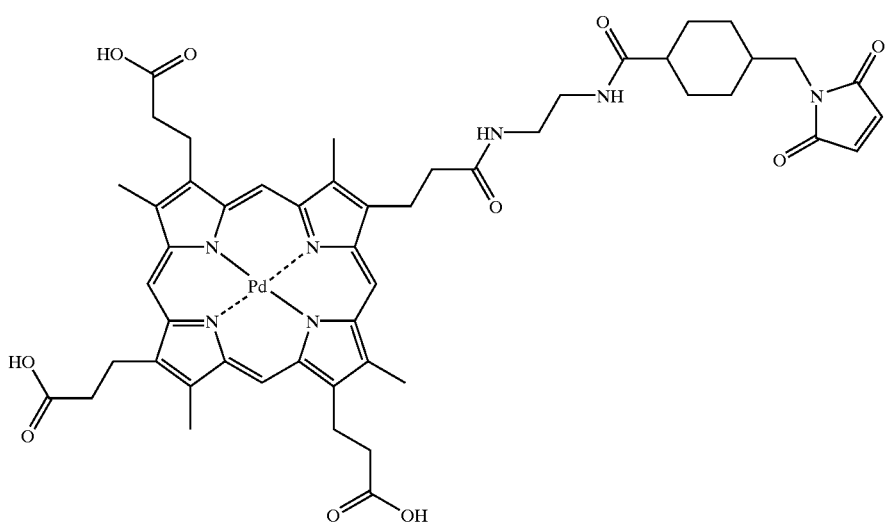
Compound 32

Compound 33
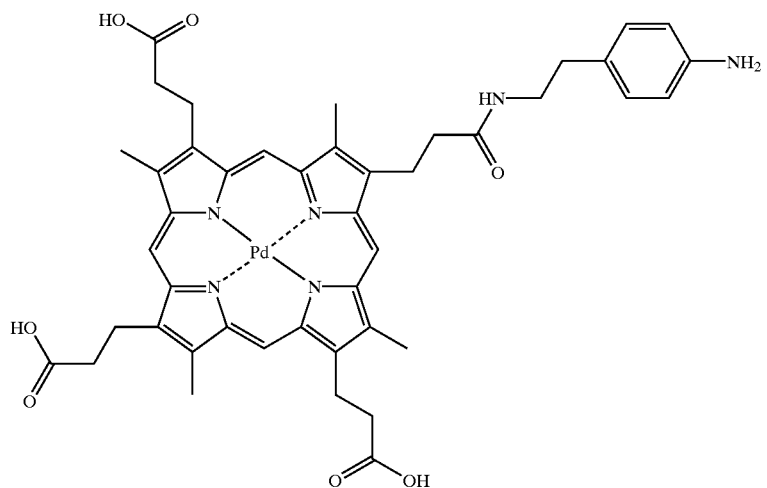
Compound 34
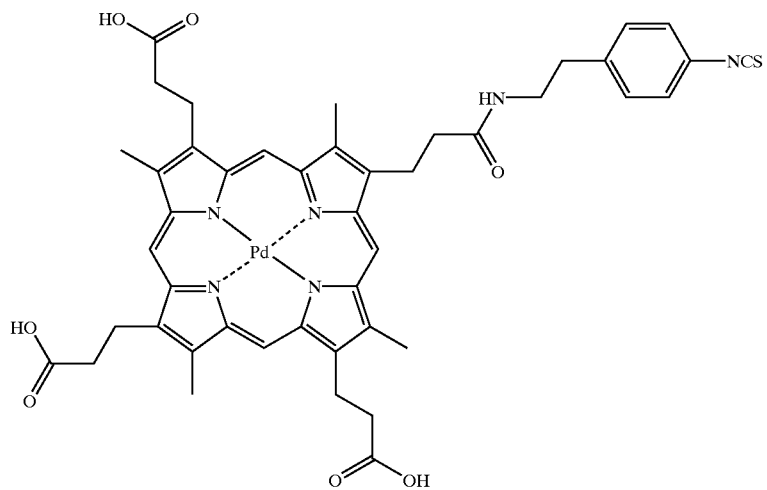
Scheme 8
Compound 35
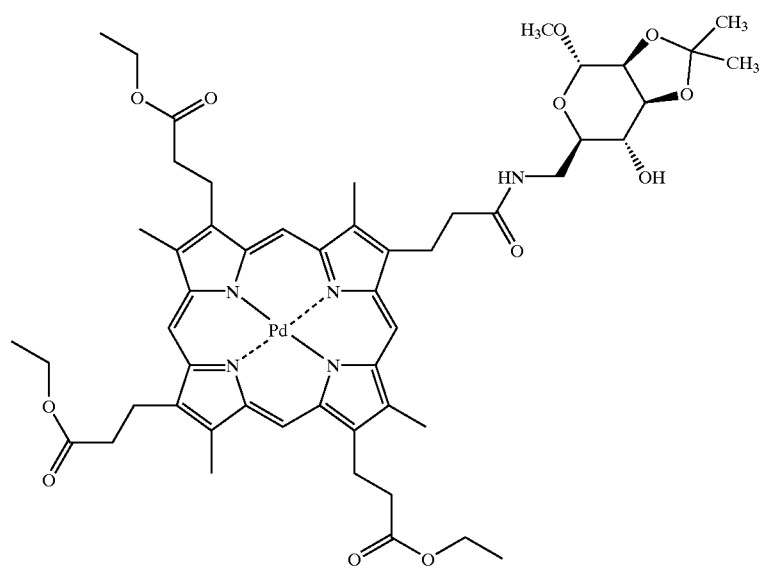

-continued
Compound 36
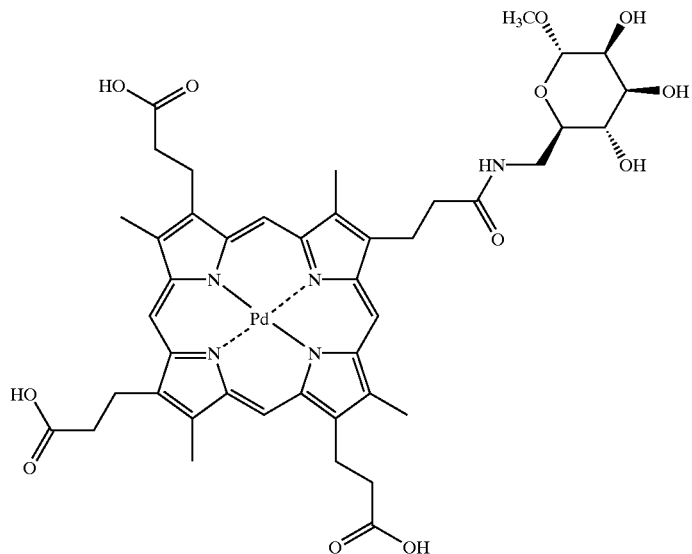
Compound 37
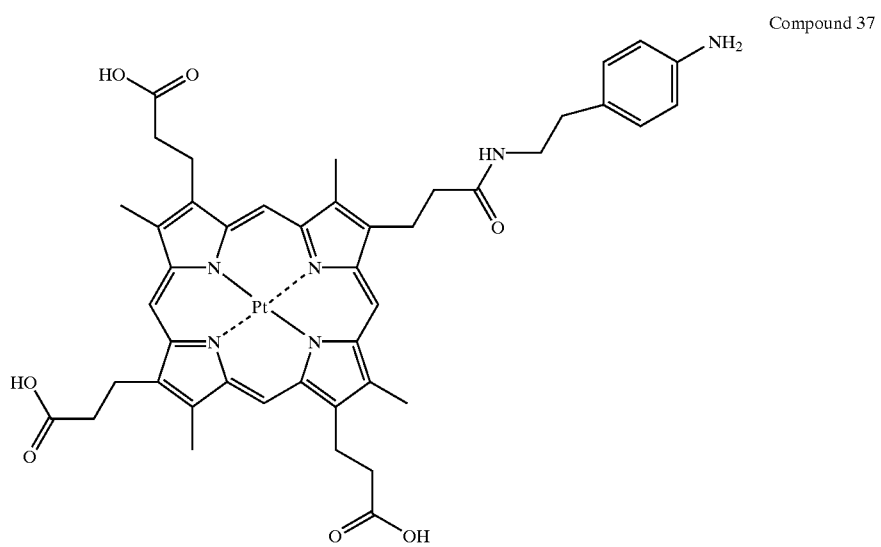
Compound 38
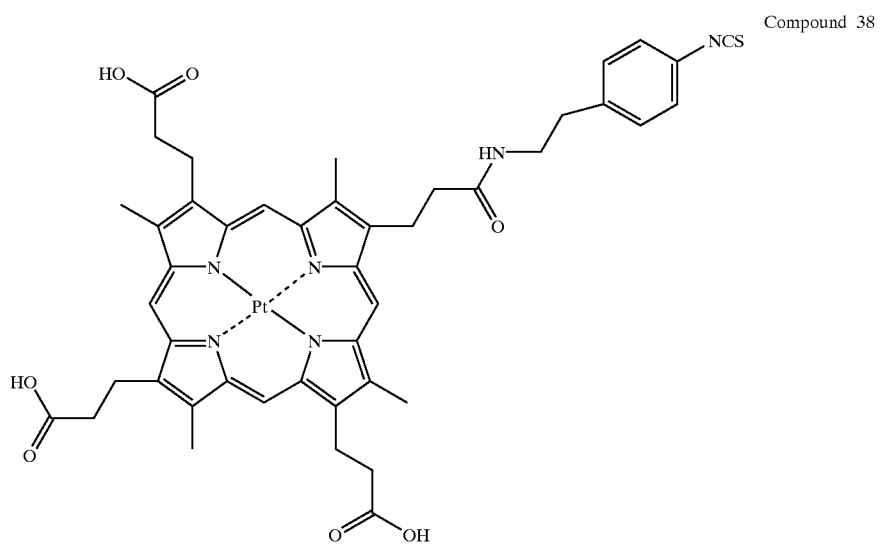

What is claimed is:

1. A substantially pure compound of formula (I) or (II):

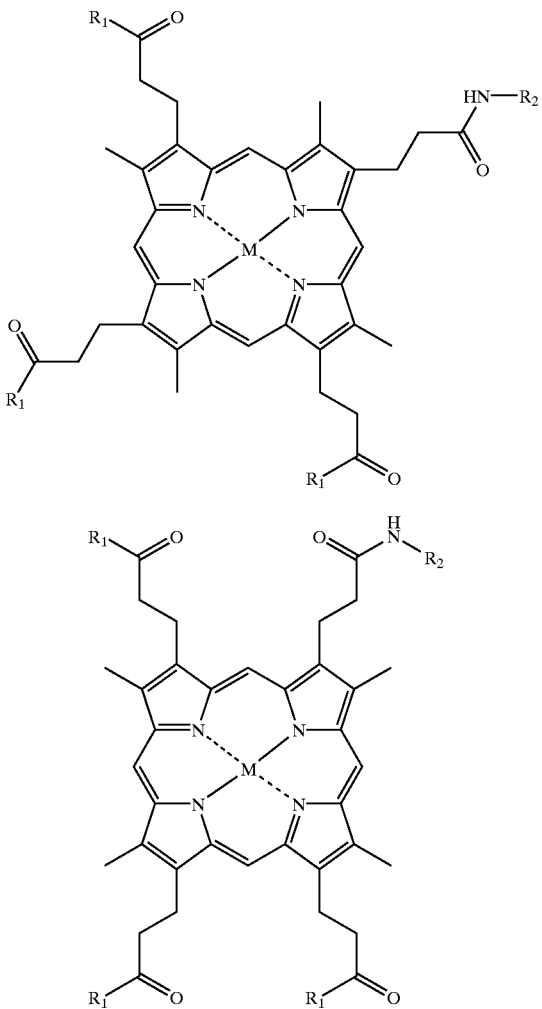

wherein

M is palladium (II) or platinum (II);

$R_1$ is —OH, —O⁻X⁺ or —OR; where R is an alkyl, an aryl, an alkyaryl group or an aralkyl group and X⁺ is a cation $R_2$ is —Y—Z, wherein
Y is either a covalent bond, a straight or branched chain alkylene, an arylene, an alkarylene or an aralkylene group, and may contain heteroatoms or side chains containing heteroatoms, or Y is a residue of a polypeptide, polysaccharide, polynucleotide or a polyether, and Z is a functional group selected from the group consisting of isothiocyanato and maleimido.

2. The compound of claim 1 wherein Y is an alkaryl group.

3. The compound of claim 1 wherein Z is a maleimido group.

4. The compound of claim 1 wherein Y is an alkaryl group and Z is an isothiocyanato group.

5. The compound of claim 1 wherein $R_1$ is —OH or —O⁻X⁺.

6. The compound of claim 1 wherein $R_1$ is —OH or —O⁻X⁺ and $R_2$ is —(CH$_2$)$_n$—Ph—NCS where Ph is a phenyl and n is an integer from 1 to 10.

7. A labelled conjugate comprising a bioaffinity reactant labelled with one or several phosphorescent labels wherein the phosphorescent label is a compound of claim 1.

8. A conjugate of claim 7 wherein the bioaffinity reactant is a biologically active molecule.

9. A bioaffinity assay method wherein at least one of the biospecific reactants is labelled with the compound of claim 1.

10. The method of claim 9 wherein the analyte is a biologically active molecule.

11. A cytological or histological staining method wherein at least one of the biospecific reactants is labelled with the compound of claim 1.

12. The conjugate of claim 8, wherein said biologically active molecule is a member of the group consisting of a hapten, a biologically active ligand, a drug, a peptide, an oligonucleotide, a nucleotide, a nucleic acid, a polypeptide, a protein, an antibody and an antibody fragment.

13. The method of claim 10, wherein said biologically active molecule is a member of the group consisting of a hapten, a biologically active ligand, a drug, a peptide, an oligonucleotide, a nucleotide, a nucleic acid, a polypeptide, a protein, an antibody and an antibody fragment.

* * * * *